(12) United States Patent
Shimizu et al.

(10) Patent No.: US 7,615,364 B2
(45) Date of Patent: Nov. 10, 2009

(54) POLYPEPTIDE HAVING ACTIVITY OF UNSATURATING W3-FATTY ACID, POLYNUCLEOTIDE CODING FOR THE POLYPEPTIDE AND USE THEREOF

(75) Inventors: Sakayu Shimizu, Kyoto (JP); Eiji Sakuradani, Kyoto (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 0 days.

(21) Appl. No.: 11/660,093

(22) PCT Filed: Aug. 19, 2005

(86) PCT No.: PCT/JP2005/015497

§ 371 (c)(1),
(2), (4) Date: Feb. 13, 2007

(87) PCT Pub. No.: WO2006/019192

PCT Pub. Date: Feb. 23, 2006

(65) Prior Publication Data

US 2008/0032335 A1 Feb. 7, 2008

(30) Foreign Application Priority Data

Aug. 20, 2004 (JP) .............................. 2004-241671

(51) Int. Cl.
- C12N 9/02 (2006.01)
- C12N 15/00 (2006.01)
- C12N 1/20 (2006.01)
- C07H 21/02 (2006.01)
- C12N 5/00 (2006.01)
- A01H 9/00 (2006.01)

(52) U.S. Cl. ................. 435/189; 435/252.3; 435/320.1; 800/4; 800/295; 536/23.1

(58) Field of Classification Search ................. 435/189, 435/252.3, 320.1; 800/8, 295; 536/23.1
See application file for complete search history.

(56) References Cited

U.S. PATENT DOCUMENTS

2006/0051847 A1* 3/2006 Gunnarsson et al. ........ 435/134

FOREIGN PATENT DOCUMENTS

WO WO 03/064596 A2 8/2003
WO WO 2005/012316 A2 2/2005
WO WO 2005/083053 A2 9/2005
WO WO 2005/118814 A2 12/2005

OTHER PUBLICATIONS

Sakuradani et al., GenEmbl Accession No. AB182163, Mar. 2005, hit #4 in the attcahed sequence search results.*
A. Shimizu, "Production of functional lipids by microorganisms," Bioscience & Industry, (2004), vol. 62, No. 1, pp. 11-16, Japanese.
A. Shimizu et al., "Metabolic engineering of oleaginous fungus, *Mortierella alpina*," Bioscience & Industry, (2001), vol. 59, No. 7, pp. 451-454, Japanese.
D. Meesapyodsuk et al., "Characterization of the Regiochemistry and Cryptoregiochemistry of a *Caenorhabditis elegans* Fatty Acid Desaturase (*FAT-1*) Expressed in *Saccharomyces cerevisiae*," Biochemistry, (2000), vol. 39, No. 39, pp. 11948-11954.
E. Sakuradani et al., "A novel fungal ω3-desaturase with wide substrate specificity from arachidonic acid-producing *Mortierella alpina* 1S-4," Appl. Microbiol. Biotechnol., (2005), vol. 66, No. 6, pp. 648-654.
Office Action issued by Chinese Patent Office in Chinese application No. 200580027907.6 issued Oct. 24, 2008 (with English-language translation).
Yao et al., "Nutrition Study of Black Gallon Seed and Oil," Guangzhou Food Industry Science & Technology, vol. 11, No. 1, p. 1 (1995) (English-language abstract).
European Search Report issued in European Application No. EP 05 77 4819 dated Jun. 16, 2008.
Oura et al., "*Saccharomyces kluyveri FAD3* encodes an ω3 fatty acid desaturase," Microbiology (2004), vol. 150, pp. 1983-1990.
Pereira et al., "A novel ω3-fatty acid desaturase involved in the biosynthesis of eicosapentaenoic acid," Biochem. J. (2004), vol. 378, pp. 665-671.
Passorn et al., "Heterologous Expression of *Mucor rouxii* $\Delta^{12}$-Desaturase Gene in *Saccharomyces cerevisiae*," Biochemical and Biophysical Research Communications (1999), vol. 263, pp. 47-51.

* cited by examiner

*Primary Examiner*—Maryam Monshipouri
(74) *Attorney, Agent, or Firm*—Drinker Biddle & Reath LLP

(57) ABSTRACT

The present invention provides a polypeptide having a wide substrate specificity and having a ω3 fatty acid desaturation activity, which makes efficiently unsaturated bond at ω3 position, and a polynucleotide coding for the same. By expressing the polypeptide in the organism, mass production of n-3 series PUFAs is enabled. Specifically, the polypeptide having a ω3 fatty acid desaturation activity and consisting of the amino acid sequence represented by SEQ ID NO: 1, a polynucleotide coding for a polypeptide having a ω3 fatty acid desaturation activity that consists of the base sequence represented by SEQ ID NO: 2 or SEQ ID NO: 3, and the like is useful for production of n-3 series fatty acids.

9 Claims, 5 Drawing Sheets

| n-3 series PUFAs | |
|---|---|
| α-linolenic acid (ALA) $18:3\Delta^{9,12,15}$ | |
| ↓ | |
| Stearidonic acid $18:4\Delta^{6,9,12,15}$ | |
| ↓ | |
| $20:4\Delta^{8,11,14,17}$ | |
| ↓ | |
| eicosapentaenoic acid (EPA) $20:5\Delta^{5,8,11,14,17}$ | |
| ↓ | |
| docosahexaenoic acid (DHA) $22:6\Delta^{4,7,10,13,16,19}$ | |

| n-6 series PUFAs | |
|---|---|
| linoleic acid (LA) $18:2\Delta^{9,12}$ | |
| ↓ | |
| γ-linolenic acid (GLA) $18:3\Delta^{6,9,12}$ | |
| ↓ | |
| dihomo-γ-linolenic acid (DGLA) $20:3\Delta^{8,11,14}$ | |
| ↓ | |
| arachidonic acid (AA or ARA) $20:4\Delta^{5,8,11,14}$ | |

18 carbons 20 carbons 22 carbons

SEQUENCE LISTING

```
<160> NUMBER OF SEQ ID NOS: 14

<210> SEQ ID NO 1
<211> LENGTH: 403
<212> TYPE: PRT
<213> ORGANISM: Mortierella alpina

<400> SEQUENCE: 1

Met Ala Pro Pro His Val Val Asp Glu Gln Val Arg Arg Ile Val
 1               5                  10                  15

Val Glu Asp Glu Ile Lys Ser Lys Lys Gln Phe Glu Arg Asn Tyr Val
                20                  25                  30

Pro Met Asp Phe Thr Ile Lys Glu Ile Arg Asp Ala Ile Pro Ala His
            35                  40                  45

Leu Phe Ile Arg Asp Thr Thr Lys Ser Ile Leu His Val Val Lys Asp
        50                  55                  60

Leu Val Thr Ile Ala Ile Val Phe Tyr Cys Ala Thr Phe Ile Glu Thr
65                  70                  75                  80

Leu Pro Ser Leu Ala Leu Arg Val Pro Ala Trp Ile Thr Tyr Trp Ile
                85                  90                  95

Ile Gln Gly Thr Val Met Val Gly Pro Trp Ile Leu Ala His Glu Cys
            100                 105                 110

Gly His Gly Ala Phe Ser Asp Ser Lys Thr Ile Asn Thr Ile Phe Gly
        115                 120                 125

Trp Val Leu His Ser Ala Leu Leu Val Pro Tyr Gln Ala Trp Ala Met
    130                 135                 140

Ser His Ser Lys His His Lys Gly Thr Gly Ser Met Thr Lys Asp Val
145                 150                 155                 160

Val Phe Ile Pro Ala Thr Arg Ser Tyr Lys Gly Leu Pro Ala Leu Glu
                165                 170                 175

Lys Pro Ala Val Glu Glu Glu Val Ser Glu Gln Glu His His His His
            180                 185                 190

Glu Glu Ser Ile Phe Ala Glu Thr Pro Ile Tyr Thr Leu Gly Ala Leu
        195                 200                 205

Leu Phe Val Leu Thr Phe Gly Trp Pro Leu Tyr Leu Ile Val Asn Phe
    210                 215                 220

Ser Gly His Glu Ala Pro His Trp Val Asn His Phe Gln Thr Val Ala
225                 230                 235                 240

Pro Leu Tyr Glu Pro His Gln Arg Lys Asn Ile Phe Tyr Ser Asn Cys
                245                 250                 255

Gly Ile Val Ala Met Gly Ser Ile Leu Thr Tyr Leu Ser Met Val Phe
            260                 265                 270

Ser Pro Leu Thr Val Phe Met Tyr Tyr Gly Ile Pro Tyr Leu Gly Val
        275                 280                 285

Asn Ala Trp Ile Val Cys Ile Thr Tyr Leu Gln His Thr Asp Pro Lys
    290                 295                 300
```

```
Val Pro His Phe Arg Asp Asn Glu Trp Asn Phe Gln Arg Gly Ala Ala
305                 310                 315                 320

Cys Thr Ile Asp Arg Ser Phe Gly Thr Ile Val Asn His Leu His His
            325                 330                 335

His Ile Gly Asp Ser His Gln Cys His His Met Phe Ser Gln Met Pro
                340                 345                 350

Phe Tyr Asn Ala Val Glu Ala Thr Lys Tyr Leu Lys Ala Lys Leu Gly
            355                 360                 365

Lys Tyr Tyr Ile Phe Asp Asp Thr Pro Ile Ala Lys Ala Leu Tyr Arg
    370                 375                 380

Asn Trp Arg Glu Cys Lys Phe Val Glu Asp Glu Gly Asp Val Val Phe
385                 390                 395                 400

Tyr Lys His

<210> SEQ ID NO 2
<211> LENGTH: 1381
<212> TYPE: DNA
<213> ORGANISM: Mortierella alpina

<400> SEQUENCE: 2
```

| | | | | | |
|---|---|---|---|---|---|
| tcataccgag | aaaatggccc | cccctcacgt | tgtcgacgaa | caagttcgac | gcaggatcgt | 60 |
| cgttgaggac | gagatcaagt | ctaagaagca | atttgagcgc | aactatgtgc | ccatggactt | 120 |
| tacgattaag | gagattcgag | atgcgatccc | tgcccacctc | ttcatccgtg | ataccacaaa | 180 |
| gtcgatcctg | catgtcgtca | aggatctggt | caccatcgcc | atcgtctttt | actgtgcaac | 240 |
| cttcattgag | actctgccct | cgctcgctct | gcgagttcct | gcctggatca | cctactggat | 300 |
| catccaagga | actgtcatgg | tcggcccctg | gatcttggct | catggtaagg | aaacgaaaaa | 360 |
| tcccatgtgt | atttctgtac | tacagaaggc | gaagtttgta | cctgaaaaga | tcagcgtcgt | 420 |
| cccttgattt | agaatgtaac | taaccttgca | atcgtatgac | ctaaattttc | ttgtgtcaac | 480 |
| gacagagtgc | ggccacggag | ctttctcgga | tagcaagacg | atcaacacca | tctttggatg | 540 |
| ggtcctccac | tctgctcttt | tggtgcccta | ccaggcctgg | gctatgtcac | actccaagca | 600 |
| tcacaagggt | actggatcga | tgaccaaaga | tgtcgttttc | atccctgcca | ctcgttccta | 660 |
| caagggcctc | ccagcactgg | agaagcctgc | cgtcgaagag | gaggtttcgg | agcaggaaca | 720 |
| ccaccaccac | gaggagtcca | tctttgccga | aactcccatc | tacacgctcg | agcgcttttt | 780 |
| gttcgtcttg | accttcggat | ggcccttgta | cttgatcgtc | aacttttcag | gacacgaggc | 840 |
| ccctcactgg | gtcaaccatt | tccagactgt | cgctcctctc | tatgagcctc | accagcgcaa | 900 |
| gaacatcttc | tactccaact | gcggcattgt | cgccatgggt | tcgatcttga | cttacctttc | 960 |
| gatggtcttc | tcgcccttga | ctgtcttcat | gtactatggc | atcccttacc | tcggagtcaa | 1020 |
| cgcctggatc | gtctgcatta | cctatctcca | gcacaccgat | cccaaggtgc | tcacttccg | 1080 |
| tgataacgag | tggaacttcc | agcgcggtgc | tgcctgcact | atcgaccgat | ccttcggtac | 1140 |
| catcgtgaac | cacctgcacc | accacattgg | cgactctcac | cagtgccacc | atatgttctc | 1200 |
| gcagatgccc | ttctacaatg | ctgtggaggc | tacaaagtac | ttgaaggcca | aacttggcaa | 1260 |
| gtactacata | tttgacgaca | cgcccattgc | caaagccctc | taccgcaatt | ggagagagtg | 1320 |
| caaattcgtg | gaggacgagg | gagatgtagt | gttttacaag | cattaacaat | ttgaatacga | 1380 |
| a | | | | | | 1381 |

```
<210> SEQ ID NO 3
```

```
<211> LENGTH: 1212
<212> TYPE: DNA
<213> ORGANISM: Mortierella alpina

<400> SEQUENCE: 3 atggccccc  ctcacgttgt  cgacgaacaa  gttcgacgca  ggatcgtcgt  tgaggacgag       60
atcaagtcta  agaagcaatt  tgagcgcaac  tatgtgccca  tggactttac  gattaaggag      120
attcgagatg  cgatccctgc  ccacctcttc  atccgtgata  ccacaaagtc  gatcctgcat      180
gtcgtcaagg  atctggtcac  catcgccatc  gtcttttact  gtgcaacctt  cattgagact      240
ctgccctcgc  tcgctctgcg  agttcctgcc  tggatcacct  actggatcat  ccaaggaact      300
gtcatggtcg  gcccctggat  cttggctcat  gagtgcggcc  acggagcttt  ctcggatagc      360
aagacgatca  acaccatctt  tggatgggtc  ctccactctg  ctcttttggt  gccctaccag      420
gcctgggcta  tgtcacactc  caagcatcac  aagggtactg  gatcgatgac  caaagatgtc      480
gttttcatcc  ctgccactcg  ttcctacaag  ggcctcccag  cactggagaa  gcctgccgtc      540
gaagaggagg  tttcggagca  ggaacaccac  caccacgagg  agtccatctt  tgccgaaact      600
cccatctaca  cgctcggagc  gcttttgttc  gtcttgacct  tcggatggcc  cttgtacttg      660
atcgtcaact  tttcaggaca  cgaggcccct  cactgggtca  accatttcca  gactgtcgct      720
cctctctatg  agcctcacca  gcgcaagaac  atcttctact  ccaactgcgg  cattgtcgcc      780
atgggttcga  tcttgactta  cctttcgatg  gtcttctcgc  ccttgactgt  cttcatgtac      840
tatggcatcc  cttacctcgg  agtcaacgcc  tggatcgtct  gcattaccta  tctccagcac      900
accgatccca  aggtgcctca  cttccgtgat  aacgagtgga  acttccagcg  cggtgctgcc      960
tgcactatcg  accgatcctt  cggtaccatc  gtgaaccacc  tgcaccacca  cattggcgac     1020
tctcaccagt  gccaccatat  gttctcgcag  atgcccttct  acaatgctgt  ggaggctaca     1080
aagtacttga  aggccaaact  tggcaagtac  tacatatttg  acgacacgcc  cattgccaaa     1140
gccctctacc  gcaattggag  agagtgcaaa  ttcgtggagg  acgagggaga  tgtagtgttt     1200
tacaagcatt  aa                                                             1212

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:Artificially
      Synthesized Primer Sequence
<220> FEATURE:
<221> NAME/KEY: modified base
<222> LOCATION: 6
<223> OTHER INFORMATION: n is inosine
<220> FEATURE:
<221> NAME/KEY: modified base
<222> LOCATION: 12
<223> OTHER INFORMATION: n is inosine

<400> SEQUENCE: 4
tgggtnytbg cncaygartg ygghca                                                 26

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:Artificially
      Synthesized Primer Sequence
<220> FEATURE:
<221> NAME/KEY: modified base
```

```
<222> LOCATION: 3
<223> OTHER INFORMATION: n is inosine
<220> FEATURE:
<221> NAME/KEY: modified base
<222> LOCATION: 9
<223> OTHER INFORMATION: n is inosine
<220> FEATURE:
<221> NAME/KEY: modified base
<222> LOCATION: 14
<223> OTHER INFORMATION: n is inosine

<400> SEQUENCE: 5
ttnggrtcng trtgytgvar raangt                                    26

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 6
gacccatcca aagatggtgt tgatc                                     25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 7
gactgtcttc atgtactatg gcatc                                     25

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 8
cagagtcata aagcttaaat ggcccccct                                 30

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 9
gacgcatgcc gtattcaaat tgttaatgc                                 29

<210> SEQ ID NO 10
<211> LENGTH: 400
<212> TYPE: PRT
<213> ORGANISM: Mortierella alpina

<400> SEQUENCE: 10

Met Ala Pro Pro Asn Thr Ile Asp Ala Gly Leu Thr Gln Arg His Ile
1               5                   10                  15

Ser Thr Ser Ala Ala Pro Thr Ser Ala Lys Pro Ala Phe Glu Arg Asn
```

```
                    20                  25                  30
Tyr Gln Leu Pro Glu Phe Thr Ile Lys Glu Ile Arg Glu Cys Ile Pro
                35                  40                  45
Ala His Cys Phe Glu Arg Ser Gly Leu Arg Gly Leu Cys His Val Ala
        50                  55                  60
Ile Asp Leu Thr Trp Ala Ser Leu Leu Phe Leu Ala Ala Thr Gln Ile
65                  70                  75                  80
Asp Lys Phe Glu Asn Pro Leu Ile Arg Tyr Leu Ala Trp Pro Ala Tyr
                85                  90                  95
Trp Ile Met Gln Gly Ile Val Cys Thr Gly Ile Trp Val Leu Ala His
                100                 105                 110
Glu Cys Gly His Gln Ser Phe Ser Thr Ser Lys Thr Leu Asn Asn Thr
                115                 120                 125
Val Gly Trp Ile Leu His Ser Met Leu Leu Val Pro Tyr His Ser Trp
        130                 135                 140
Arg Ile Ser His Ser Lys His His Lys Ala Thr Gly His Met Thr Lys
145                 150                 155                 160
Asp Gln Val Phe Val Pro Lys Thr Arg Ser Gln Val Gly Leu Pro Pro
                165                 170                 175
Lys Glu Asn Val Ala Val Ala Val Gln Glu Glu Asp Met Ser Val His
                180                 185                 190
Leu Asp Glu Glu Ala Pro Ile Val Thr Leu Phe Trp Met Val Ile Gln
        195                 200                 205
Phe Leu Phe Gly Trp Pro Ala Tyr Leu Ile Met Asn Ala Ser Gly Gln
        210                 215                 220
Asp Tyr Gly Arg Trp Thr Ser His Phe His Thr Tyr Ser Pro Ile Phe
225                 230                 235                 240
Glu Pro Arg Asn Phe Phe Asp Ile Ile Ile Ser Asp Leu Gly Val Leu
                245                 250                 255
Ala Ala Leu Gly Thr Leu Ile Tyr Ala Ser Met Gln Leu Ser Leu Leu
                260                 265                 270
Thr Val Thr Lys Tyr Tyr Ile Val Pro Tyr Leu Phe Val Asn Phe Trp
        275                 280                 285
Leu Val Leu Ile Thr Phe Leu Gln His Thr Asp Pro Lys Leu Pro His
        290                 295                 300
Tyr Arg Glu Gly Ala Trp Asn Phe Gln Arg Gly Ala Leu Cys Thr Val
305                 310                 315                 320
Asp Arg Ser Phe Gly Lys Phe Leu Asp His Met Phe His Gly Ile Val
                325                 330                 335
His Thr His Val Ala His His Leu Phe Ser Gln Met Pro Phe Tyr His
                340                 345                 350
Ala Glu Glu Ala Thr His His Leu Lys Lys Leu Leu Gly Glu Tyr Tyr
                355                 360                 365
Val Tyr Asp Pro Ser Pro Ile Val Val Ala Val Trp Arg Ser Phe Arg
        370                 375                 380
Glu Cys Arg Phe Val Glu Asp His Gly Asp Val Val Phe Phe Lys Lys
385                 390                 395                 400

<210> SEQ ID NO 11
<211> LENGTH: 419
<212> TYPE: PRT
<213> ORGANISM: Saccharomyces kluyveri

<400> SEQUENCE: 11
```

-continued

```
Met Ser Ile Glu Thr Val Gly Ser Ser Val Ala Ile Asn Ser
 1               5              10              15

Lys Ala Val Ser Ser Thr Ala Thr Thr Val Val Gln Pro Lys Thr Ala
                 20                  25                  30

Ile Asp Thr Asn Gly Asn Val Phe Lys Val Pro Asp Tyr Thr Ile Lys
             35                  40                  45

Asp Ile Leu Ser Ala Ile Pro Lys Glu Cys Tyr Lys Arg Asp Thr Leu
         50                  55                  60

Trp Ser Leu His Tyr Val Val Arg Asp Ile Ala Ala Ile Leu Val Ile
 65                  70                  75                  80

Gly Tyr Leu Gly Thr Asn Tyr Ile Pro Val Leu Phe Pro Asn Ser Ala
                 85                  90                  95

Leu Leu Arg Gly Ile Ala Tyr Ala Ile Gln Ser Tyr Leu Ile Gly Leu
            100                 105                 110

Phe Gly Phe Gly Leu Trp Ile Leu Ala His Glu Cys Gly His Ser Ala
        115                 120                 125

Phe Ser Glu Ser Asn Ala Val Asn Asp Thr Val Gly Trp Val Leu His
    130                 135                 140

Ser Trp Trp Met Val Pro Tyr Phe Pro Trp Lys Phe Ser His Ser Lys
145                 150                 155                 160

His His Lys Ala Thr Gly His Met Thr Arg Asp Met Val Phe Ile Pro
                165                 170                 175

Tyr Thr Lys Asp Glu Phe Ile Thr Met Lys Lys Ser Lys Phe Ala
            180                 185                 190

Glu Ile Thr Glu Glu Ala Pro Val Met Thr Leu Phe Asn Leu Ile Ala
        195                 200                 205

Gln Gln Val Gly Gly Leu Gln Leu Tyr Leu Ala Thr Asn Ala Thr Gly
    210                 215                 220

Gln Pro Tyr Pro Gly Val Lys Lys Phe Phe Lys Ser His Tyr Trp Pro
225                 230                 235                 240

Thr Ser Pro Val Phe Asp Ala Lys Asp Phe Trp Ile Ile Met Ser
                245                 250                 255

Asp Ile Gly Ile Val Ser Thr Leu Leu Ile Asn Tyr Leu Trp Tyr Arg
            260                 265                 270

Ala Tyr Gly Ala His Val Val Leu Ile Asn Trp Phe Ile Pro Trp Leu
        275                 280                 285

Trp Val Asn His Trp Leu Val Phe Val Thr Phe Leu Gln His Thr Asp
    290                 295                 300

Pro Thr Met Pro His Tyr Asp Ala Glu Glu Trp Thr Phe Ala Lys Gly
305                 310                 315                 320

Ala Ala Ala Thr Ile Asp Arg Asn Phe Gly Phe Val Gly Gln His Ile
                325                 330                 335

Phe His Asp Ile Ile Glu Thr His Val Leu His His Tyr Cys Ser Arg
            340                 345                 350

Ile Pro Phe Tyr Asn Ala Arg Lys Ala Thr Ser Ala Ile Lys Glu Val
        355                 360                 365

Met Gly Gln His Tyr Arg Tyr Glu Gly Glu Asn Met Trp Lys Ser Leu
    370                 375                 380

Trp Lys Val Ala Arg Ser Cys Gln Tyr Val Glu Gly Asp Asn Gly Val
385                 390                 395                 400

Arg Met Phe Arg Asn Thr Asn Gly Val Gly Val Lys Pro Glu Asp Gly
                405                 410                 415

Ser Ser Gln
```

<210> SEQ ID NO 12
<211> LENGTH: 416
<212> TYPE: PRT
<213> ORGANISM: Saccharomyces kluyveri

<400> SEQUENCE: 12

```
Met Ser Ala Val Thr Val Thr Gly Ser Asp Pro Lys Asn Arg Gly Ser
  1               5                  10                  15

Ser Ser Asn Thr Glu Gln Glu Val Pro Lys Val Ala Ile Asp Thr Asn
             20                  25                  30

Gly Asn Val Phe Ser Val Pro Asp Phe Thr Ile Lys Asp Ile Leu Gly
         35                  40                  45

Ala Ile Pro His Glu Cys Tyr Glu Arg Arg Leu Ala Thr Ser Leu Tyr
     50                  55                  60

Tyr Val Phe Arg Asp Ile Phe Cys Met Leu Thr Thr Gly Tyr Leu Thr
 65                  70                  75                  80

His Lys Ile Leu Tyr Pro Leu Leu Ile Ser Tyr Thr Asn Ser Ile
                 85                  90                  95

Ile Lys Phe Thr Phe Trp Ala Leu Tyr Thr Tyr Val Gln Gly Leu Phe
                100                 105                 110

Gly Thr Gly Ile Trp Val Leu Ala His Glu Cys Gly His Gln Ala Phe
            115                 120                 125

Ser Asp Tyr Gly Ile Val Asn Asp Phe Val Gly Trp Thr Leu His Ser
130                 135                 140

Tyr Leu Met Val Pro Tyr Phe Ser Trp Lys Tyr Ser His Gly Lys His
145                 150                 155                 160

His Lys Ala Thr Gly His Met Thr Arg Asp Met Val Phe Val Pro Ala
                165                 170                 175

Thr Lys Glu Glu Phe Lys Lys Ser Arg Asn Phe Phe Gly Asn Leu Ala
            180                 185                 190

Glu Tyr Ser Glu Asp Ser Pro Leu Arg Thr Leu Tyr Glu Leu Leu Val
        195                 200                 205

Gln Gln Leu Gly Gly Trp Ile Ala Tyr Leu Phe Val Asn Val Thr Gly
    210                 215                 220

Gln Pro Tyr Pro Asp Val Pro Ser Trp Lys Trp Asn His Phe Trp Leu
225                 230                 235                 240

Thr Ser Pro Leu Phe Glu Gln Arg Asp Ala Leu Tyr Ile Phe Leu Ser
                245                 250                 255

Asp Leu Gly Ile Leu Thr Gln Gly Ile Val Leu Thr Leu Trp Tyr Lys
            260                 265                 270

Lys Phe Gly Gly Trp Ser Leu Phe Ile Asn Trp Phe Val Pro Tyr Ile
        275                 280                 285

Trp Val Asn His Trp Leu Val Phe Ile Thr Phe Leu Gln His Thr Asp
    290                 295                 300

Pro Thr Met Pro His Tyr Asn Ala Glu Glu Trp Thr Phe Ala Lys Gly
305                 310                 315                 320

Ala Ala Ala Thr Ile Asp Arg Lys Phe Gly Phe Ile Gly Pro His Ile
                325                 330                 335

Phe His Asp Ile Ile Glu Thr His Val Leu His His Tyr Cys Ser Arg
            340                 345                 350

Ile Pro Phe Tyr Asn Ala Arg Pro Ala Ser Glu Ala Ile Lys Lys Val
        355                 360                 365

Met Gly Lys His Tyr Arg Ser Ser Asp Glu Asn Met Trp Lys Ser Leu
```

```
                  370                 375                 380
Trp Lys Ser Phe Arg Ser Cys Gln Tyr Val Asp Gly Asp Asn Gly Val
385                 390                 395                 400

Leu Met Phe Arg Asn Ile Asn Asn Cys Gly Val Gly Ala Ala Glu Lys
                405                 410                 415

<210> SEQ ID NO 13
<211> LENGTH: 380
<212> TYPE: PRT
<213> ORGANISM: Glycine max

<400> SEQUENCE: 13

Met Val Lys Asp Thr Lys Pro Leu Ala Tyr Ala Ala Asn Asn Gly Tyr
 1               5                  10                  15

Gln Gln Lys Gly Ser Ser Phe Asp Phe Asp Pro Ser Ala Pro Pro Pro
                20                  25                  30

Phe Lys Ile Ala Glu Ile Arg Ala Ser Ile Pro Lys His Cys Trp Val
            35                  40                  45

Lys Asn Pro Trp Arg Ser Leu Ser Tyr Val Leu Arg Asp Val Leu Val
 50                  55                  60

Ile Ala Ala Leu Val Ala Ala Ile His Phe Asp Asn Trp Leu Leu
 65                  70                  75                  80

Trp Leu Ile Tyr Cys Pro Ile Gln Gly Thr Met Phe Trp Ala Leu Phe
                85                  90                  95

Val Leu Gly His Asp Cys Gly His Gly Ser Phe Ser Asp Ser Pro Leu
            100                 105                 110

Leu Asn Ser Leu Val Gly His Ile Leu His Ser Ser Ile Leu Val Pro
        115                 120                 125

Tyr His Gly Trp Arg Ile Ser His Arg Thr His His Gln Asn His Gly
    130                 135                 140

His Ile Glu Lys Asp Glu Ser Trp Val Pro Leu Thr Glu Lys Ile Tyr
145                 150                 155                 160

Lys Asn Leu Asp Ser Met Thr Arg Leu Ile Arg Phe Thr Val Pro Phe
                165                 170                 175

Pro Leu Phe Val Tyr Pro Ile Tyr Leu Phe Ser Arg Ser Pro Gly Lys
            180                 185                 190

Glu Gly Ser His Phe Asn Pro Tyr Ser Asn Leu Phe Pro Pro Ser Glu
        195                 200                 205

Arg Lys Gly Ile Ala Ile Ser Thr Leu Cys Trp Ala Thr Met Phe Ser
    210                 215                 220

Leu Leu Ile Tyr Leu Ser Phe Ile Thr Ser Pro Leu Leu Val Leu Lys
225                 230                 235                 240

Leu Tyr Gly Ile Pro Tyr Trp Ile Phe Val Met Trp Leu Asp Phe Val
                245                 250                 255

Thr Tyr Leu His His His Gly His His Gln Lys Leu Pro Trp Tyr Arg
            260                 265                 270

Gly Lys Glu Trp Ser Tyr Leu Arg Gly Gly Leu Thr Thr Val Asp Arg
        275                 280                 285

Asp Tyr Gly Trp Ile Tyr Asn Ile His His Asp Ile Gly Thr His Val
    290                 295                 300

Ile His His Leu Phe Pro Gln Ile Pro His Tyr His Leu Val Glu Ala
305                 310                 315                 320

Thr Gln Ala Ala Lys Pro Val Leu Gly Asp Tyr Tyr Arg Glu Pro Glu
                325                 330                 335
```

-continued

Arg Ser Ala Pro Leu Pro Phe His Leu Ile Lys Tyr Leu Ile Gln Ser
            340                 345                 350

Met Arg Gln Asp His Phe Val Ser Asp Thr Gly Asp Val Val Tyr Tyr
            355                 360                 365

Gln Thr Asp Ser Leu Leu Leu His Ser Gln Arg Asp
            370                 375             380

<210> SEQ ID NO 14
<211> LENGTH: 453
<212> TYPE: PRT
<213> ORGANISM: Glycine max

<400> SEQUENCE: 14

Met Ala Thr Trp Tyr His Gln Lys Cys Gly Leu Lys Pro Leu Ala Pro
  1               5                  10                  15

Val Ile Pro Arg Pro Arg Thr Gly Ala Ala Leu Ser Ser Thr Ser Arg
             20                  25                  30

Val Glu Phe Leu Asp Thr Asn Lys Val Val Ala Gly Pro Lys Phe Gln
         35                  40                  45

Pro Leu Arg Cys Asn Leu Arg Glu Arg Asn Trp Gly Leu Lys Val Ser
     50                  55                  60

Ala Pro Leu Arg Val Ala Ser Ile Glu Glu Gln Lys Ser Val Asp
 65                  70                  75                  80

Leu Thr Asn Gly Thr Asn Gly Val Glu His Glu Lys Leu Pro Glu Phe
                 85                  90                  95

Asp Pro Gly Ala Pro Pro Phe Asn Leu Ala Asp Ile Arg Ala Ala
            100                 105                 110

Ile Pro Lys His Cys Trp Val Lys Asp Pro Trp Arg Ser Met Ser Tyr
            115                 120                 125

Val Val Arg Asp Val Ile Ala Val Phe Gly Leu Ala Ala Ala Ala Ala
130                 135                 140

Tyr Leu Asn Asn Trp Leu Val Trp Pro Leu Tyr Trp Ala Ala Gln Gly
145                 150                 155                 160

Thr Met Phe Trp Ala Leu Phe Val Leu Gly His Asp Cys Gly His Gly
                165                 170                 175

Ser Phe Ser Asn Asn Ser Lys Leu Asn Ser Val Val Gly His Leu Leu
            180                 185                 190

His Ser Ser Ile Leu Val Pro Tyr His Gly Trp Arg Ile Ser His Arg
            195                 200                 205

Thr His His Gln His His Gly His Ala Glu Asn Asp Glu Ser Trp His
            210                 215                 220

Pro Leu Pro Glu Lys Leu Phe Arg Ser Leu Asp Thr Val Thr Arg Met
225                 230                 235                 240

Leu Arg Phe Thr Ala Pro Phe Pro Leu Leu Ala Phe Pro Val Tyr Leu
                245                 250                 255

Phe Ser Arg Ser Pro Gly Lys Thr Gly Ser His Phe Asp Pro Ser Ser
            260                 265                 270

Asp Leu Phe Val Pro Asn Glu Arg Lys Asp Val Ile Thr Ser Thr Ala
            275                 280                 285

Cys Trp Ala Ala Met Leu Gly Leu Leu Val Gly Leu Gly Phe Val Met
            290                 295                 300

Gly Pro Ile Gln Leu Leu Lys Leu Tyr Gly Val Pro Tyr Val Ile Phe
305                 310                 315                 320

Val Met Trp Leu Asp Leu Val Thr Tyr Leu His His Gly His Glu
                325                 330                 335

-continued

```
Asp Lys Leu Pro Trp Tyr Arg Gly Lys Glu Trp Ser Tyr Leu Arg Gly
            340             345             350

Gly Leu Thr Thr Leu Asp Arg Asp Tyr Gly Trp Ile Asn Asn Ile His
            355             360             365

His Asp Ile Gly Thr His Val Ile His His Leu Phe Pro Gln Ile Pro
        370             375             380

His Tyr His Leu Val Glu Ala Thr Glu Ala Ala Lys Pro Val Phe Gly
385                 390             395                 400

Lys Tyr Tyr Arg Glu Pro Lys Lys Ser Ala Ala Pro Leu Pro Phe His
            405             410             415

Leu Ile Gly Glu Ile Ile Arg Ser Phe Lys Thr Asp His Phe Val Ser
            420             425             430

Asp Thr Gly Asp Val Val Tyr Tyr Gln Thr Asp Ser Lys Ile Asn Gly
            435             440             445

Ser Ser Lys Leu Glu
        450
```

POLYPEPTIDE HAVING ACTIVITY OF UNSATURATING W3-FATTY ACID, POLYNUCLEOTIDE CODING FOR THE POLYPEPTIDE AND USE THEREOF

CROSS REFERENCE TO RELATED APPLICATIONS

This application is the National Stage of International Application No. PCT/JP2005/015497 filed Aug. 19, 2005, and claims benefit of Japanese Application No. 2004-241671 filed Aug. 20, 2004, which are incorporated herein in their entirety.

REFERENCE TO A SEQUENCE LISTING

A Sequence Listing containing SEQ ID NOS:1-14 is incorporated herein by reference.

TECHNICAL FIELD

The present invention relates to a polypeptide having a ω3 fatty acid desaturation activity and catalyzing a synthetic reaction of n-3 series unsaturated fatty acid, a polynucleotide coding for the same, and typical use thereof.

BACKGROUND ART

Polyunsaturated fatty acids (PUFAs) plays an important role in the organism as a constituent of the cell membrane phosphatide, as well as a precursor of the hormone-like physiologically active substance such as prostagrandin, thromboxane, leukotriene and the like. The physiologically active substance, which is synthesized from PUFAs, is called eicosanoid. Eicosanoid is synthesized as needed in the body, and regulates inflammatory reaction, reproduction function, immunological response, blood pressure and the like. In addition as for PUFAs, it has been reported that it is necessary for the cerebral development of the infant.

The PUFAs is classified into series called n-3, n-6, n-9 and the like along the route of biosyntheses. Herein, the numeral "3", "6", and "9" following "n-" shows in which number of carbon the first double bond is present from the methyl group of PUFAs. For example, the "n-3" series shows PUFAs, wherein the first double bond from the methyl group is present in the third carbon when the carbon of the methyl group is made a carbon in first position, and it is assumed second position, third position and so on, one by one toward the carboxyl group side, and is displayed as ω3 series. In FIG. 7, major n-3 and n-6 series PUFAs in animal are shown. In n-3 (ω3) series, α-linolenic acid, which is an essential fatty acid, stearidonic acid, $20:4\Delta^{8,11,14,17}$, eicosapentaenoic acid (EPA), and docosahexaenoic acid (DHA), etc., which are a metabolite from α-linolenic acid (ALA) in vivo, are included. Moreover, n-6 (ω6) series includes linoleic acid (LA), which is an essential fatty acid, and γ-linolenic acid (GLA), dihomo-γ-linolenic acid (DGLA), arachidonic acid (AA or ARA), etc., Which are a metabolite from linoleic acid in vivo. For example, "18:2" in the indication represented by "$18:2\Delta^{9,12}$" shows that the number of carbons is 18 and the number of double bonds is two. Moreover, "$\Delta^{9,12}$" shows the position of double bond when the carbon of the carboxyl group is made a carbon in first position, and it is assumed second position, third position and so on, one by one toward the methyl group. In addition, since animals cannot desaturate C—C bond on methyl group over $\Delta^9$ position, they have to take Q-linolenic acid and linoleic acid from food (vegetable food) as an essential fatty acid, and cannot convert n-6 series to n-3, or n-3 series to n-6, interchangeably.

It is well known that n-6 and n-3 series PUFAs function differently. Indeed, both play an important role in the body. For n-3 series PUFAs, it is known that there have a lot of physiological activities commencing with antithrombotic action and improvement of serum lipid for EPA, and improvement of learning function and anticancer action for DHA. The n-3 series PUFAs are essential for maintaining homeostasis. As described above, since the animals cannot synthesize n-3 series PUFAs in vivo, it is very important for them to take n-3 series PUFAs orally.

As mentioned above, to synthesize n-3 series PUFAs, which importance is recently pointed out, ω3 fatty acid desaturase having an activity that generates ω3 unsaturated fatty acid by forming unsaturated bond between the third and the fourth positions from methyl group of fatty acid, i.e., ω3 and ω4 positions, is necessary. The gene for ω3 fatty acid desaturase has been cloned so far in higher plant, green algae, C. elegans, oomycetes, ascomycetes and the like (for example, see Japanese Patent Application Laid-Open (Kokai) No. 2001-95588 (published on Apr. 10, 2001); International Publication W003/064596 (published on Aug. 7, 2003); Science 258: 1353-1355 (1992); Biosci. Biotechnol. Biochem. 66: 1314-1327 (2002); Proc. Natl. Acad. Sci. USA, 94: 1142-1147 (1997); Biochemistry 39: 11948-11954 (2000); Biochem. J. 378: 665-671 (2004); Microbiology 150: 1983-1990 (2004); and Biochem. Biophys. Res. Commun. 150: 335-341 (1988)).

In Japanese Patent Application Laid-Open (Kokai) No. 2001-95588, Science 258: 1353-1355 (1992) and Biosci. Biotechnol. Biochem. 66: 1314-1327 (2002), it has been reported that the protein that is encoded by ω3 fatty acid desaturase gene of higher plants and/or green algae has an activity, which converts n-6 series fatty acid such as linoleic acid (18:2) having 18 carbons to n-3 series such as α-linolenic acid (18:3). However, the protein that is encoded by ω3 fatty acid desaturase gene of higher plants and green algae cannot convert a fatty acid having 20 carbons to n-3 series fatty acid.

In Proc. Natl. Acad. Sci. USA, 94: 1142-1147 (1997) and Biochemistry 39: 11948-11954 (2000), it has been reported that the proteins that is encoded by ω3 fatty acid desaturase gene (FAT-1) of Caenorhabditis elegans (C. elegans) acts on n-6 series fatty acid having 16-20 carbons and generate unsaturated bond at the ω3 position. However, in Biochemistry 39: 11948-11954 (2000), it has been reported that when this ω3 fatty acid desaturase gene is expressed in yeast, the conversion rate from arachidonic acid (20:4), which is n-6 series fatty acid, to eicosapentaenoic acid (EPA) (20:5), which is n-3 series fatty acid, is low, being only 1.9%.

Moreover, in International Publication WO03/064596, Japanese Patent Application Laid-Open (Kokai) No. 2001-95588 and Biochem. J. 378: 665-671 (2004), the protein that is encoded by ω3 fatty acid desaturase gene (SDD17) of oomycetes (Saprolegnia diclina) acts on n-6 series fatty acid having 20 carbons and generates unsaturated bond at the ω3 position. However, on the contrary, it cannot make the ω3 position of n-6 fatty acid having 18 carbons unsaturated.

Moreover, in Microbiology 150: 1983-1990 (2004), it has been reported that ω3 fatty acid desaturase gene was cloned from Saccharomyces kluyveri, which belongs to ascomycetes. The protein that is encoded by this gene has an activity converting linoleic acid (18:2), which is n-6 series, to α-linolenic acid (18:3), which is n-3 series. However, on the contrary, the ω3 fatty acid desaturase cannot make the ω3 position of n-6 fatty acid having 20 carbons unsaturated.

Meanwhile, it is known that when *Mortierella alpina*, which is a lipid production fungi, is stood in the condition of low temperature, it generates eicosapentaenoic acid (EPA). That is, eicosapentaenoic acid is not generated when *M. alpina* is cultured at 25° C., but generated when cultured at 11° C. using glucose as a carbon source (see, for example, Biochem. Biophys. Res. Commun. 150: 335-341 (1988)). From this result, it is suggested that there is ω3 fatty acid desaturase, wherein its gene expression is induced or activated under condition of low temperature.

Moreover, it is known that eicosapentaenoic acid is accumulated in the fungus cells when many strain of *Mortierella* subgenera is cultured at the low temperature. In that case, since no n-3 series fatty acid other than eicosapentaenoic acid (EPA) was detected, it was considered that eicosapentaenoic acid (EPA) was generated by unsaturation of ω3 position of arachidonic acid under the low temperature condition (see J Am Oil Chem Soc 65, 1455-1459 (1988)). From this result, it is strongly suggested that ω3 fatty acid desaturase, which makes fatty acids having 20 carbons unsaturated, exists.

DISCLOSURE OF THE INVENTION

As described above, it has been reported until now that ω3 fatty acid desaturase gene is cloned in higher plants, green algae, *C. elegans*, oomycetes, ascomycetes and the like. However, the ω3 fatty acid desaturase gene that had been reported so far had problems as follows: substrates to be made unsaturated at ω3 position are limited to fatty acid having specific number of carbons; or efficiency of unsaturation is low even if introducing the gene into the host cell and expressing the gene. If the ω3 fatty acid desaturase gene to act on the fatty acid within the wider range, and to generate the unsaturated bond at the ω3 position efficiently can be acquired, various kinds of n-3 series fatty acid can be synthesized more efficiently.

In addition, the ω3 fatty acid desaturase derived from the *S. kluyveri*, only one species among fungi, whose gene has been cloned, cannot make fatty acids having 20 carbons unsaturated. On the other hand, as described above, it is suggested that ω3 fatty acid desaturase exists in the strain of Mortierella a subgenus. However, the gene coding for the desaturase is not acquired yet. It is considered that it is difficult to clone the ω3 fatty acid desaturase gene derived from *M. alpina* with degenerate primers designed by comparisons of sequences for such a known ω3 fatty acid desaturase.

The present invention is made considering the above-mentioned problems, and intends to provide a polypeptide having a ω3 fatty acid desaturation activity, which acts on a greater range of fatty acids and further, generates unsaturated bond at ω3 position efficiently, and a polynucleotide coding for the same.

In order to solve the above-mentioned problems, the inventors made extensive studies and as a result, since, in *S. kluyveri*, only one species among fungi, whose ω3 fatty acid desaturase gene has been cloned, (i) the amino acid sequence of ω3 fatty acid desaturase derived from *S. kluyveri* has the highest homology (60%) to that of $\Delta^{12}$ fatty acid desaturase of *S. kluyveri* own, and (ii) the amino acid sequence of ω3 fatty acid desaturase derived from *S. kluyveri* has also high homology (38.6%) to that of $\Delta^{12}$ fatty acid desaturase of *M. alpina* (see Microbiology 150: 1983-1990 (2004)), it was assumed that in *M. alpina*, there is a possibility that the homology of the amino acid sequences between ω3 fatty acid desaturase and $\Delta^{12}$ fatty acid desaturase is high also. Then, the inventors designed primers by comparison of the deduced amino acid sequences for $\Delta^{12}$ fatty acid desaturase from *M. alpina*, $\Delta^{12}$ fatty acid desaturase from *S. kluyveri*, and ω3 fatty acid desaturase from *S. kluyveri*. Using these primers, the inventors succeeded in the acquisition of the ω3 fatty acid desaturase gene of *M. alpina* by PCR. Moreover, when the obtained ω3 fatty acid desaturase gene was actually expressed in the organism, the inventors found that the enzyme can act on all n-6 series fatty acid having 18 and 20 carbons and generate unsaturated bond at the ω3 position efficiently. Based on these findings, the inventors have accomplished the present invention.

That is, the polypeptide according to the present invention is a polypeptide having a ω3 fatty acid desaturation activity, which is characterized by (a) or (b) described below:
(a) a polypeptide consisting of the amino acid sequence represented by SEQ ID NO: 1;
(b) a polypeptide consisting of an amino acid sequence, wherein one or plural amino acids are substituted, deleted, inserted or added in the amino acid sequence represented by SEQ ID NO: 1.

According to the above-mentioned constitution, the polypeptide according to the present invention can catalyze ω3 unsaturated fatty acid synthesis reaction.

The antibody according to the present invention is characterized by binding to the above-mentioned polypeptide.

According to the above-mentioned constitution, the antibody of the present invention can identify an organism, or a tissue or a cell therefrom, wherein a polypeptide having ω3 fatty acid desaturation activity is expressed.

The polynucleotide according to the present invention is characterized by coding for the above-mentioned polypeptide.

Moreover, the polynucleotide of the present invention is a polynucleotide coding for a polypeptide having a ω3 fatty acid desaturation activity, and preferred is any of (c), (d), (e) or (f) described below:
(c) a polynucleotide consisting of the base sequence represented by SEQ ID NO: 2 or SEQ ID NO: 3;
(d) a polynucleotide consisting of the base sequence from 14 to 1366 of the base sequence represented by SEQ ID NO: 2;
(e) a polynucleotide, which hybridizes with a polynucleotide consisting of a complementary base sequence to the base sequence represented by SEQ ID NO: 2 or SEQ ID NO: 3 under stringent conditions;
(f) a polynucleotide, which hybridizes with a polynucleotide consisting of a complementary base sequence to the base sequence from 14 to 1366 of the base sequence represented by SEQ ID NO: 2.

According to the above-mentioned constitution, to synthesize the polypeptide having ω3 fatty acid desaturation activity in transformant, the above-mentioned polynucleotide can be used.

The vector of the present invention is characterized by comprising the above-mentioned polynucleotide.

According to the above-mentioned constitution, the polynucleotide described above can be introduced into organism or cell to express the polypeptide having ω3 fatty acid desaturation activity recombinantly, or using cell-free protein synthesis system, the polypeptide having ω3 fatty acid desaturation activity can be synthesized.

The transformant according to the present invention is characterized in the fact that the above-mentioned polynucleotide has been introduced. The above-mentioned transformant is preferably fungi (yeasts, filamentous fungi), animals, plants or progeny thereof, or a cell or tissue therefrom. Further, the above-mentioned plant is preferably soybean, rapeseed, sesame, olive, linseed, maize, sunflower or safflower. In addition, in transformant, the fatty acid composition is preferably modified.

The method for producing the above-mentioned polypeptide according to the present invention is characterized by using the above-mentioned vector. Moreover, the method for producing the above-mentioned polypeptide according to the present invention may use the above-mentioned transformant.

According to the above-mentioned constitution, under conditions of low costs and reduced load against environment, the polypeptide catalyzing desaturation of ω3 fatty acid can be provided.

The method for producing fatty acid according to the present invention is characterized by using the above-mentioned transformant.

Moreover, using the method for producing the above-mentioned polypeptide according to the present invention, the polypeptide can be produced by culturing the transformant, into which the above-mentioned polynucleotide has been introduced, at a temperature that is lower than the optimal culture temperature, from the beginning of culture or after culturing at the optimal culture temperature; or, the above-mentioned polypeptide can be produced by exposing a synthesis system of the above-mentioned polypeptide on the temperature condition from 0° C. up to 20° C. Further, a temperature that is lower than the optimal culture temperature, which is described above, may be between 0° C. and 20° C.

In the method for producing the fatty acid according to the present invention, preferred is a method comprising culturing the organisms or the cells, into which the above-mentioned polynucleotide has been introduced, at a temperature that is lower than the optimal culture temperature, from the beginning of culture or after culturing at the optimal culture temperature and producing the fatty acid. Moreover, preferred is a temperature from 0° C. up to 20° C. as a temperature that is lower than the optimal culture temperature, which is described above.

According to the above-mentioned constitution, the polypeptide catalyzing ω3 fatty acid desaturation reaction can be functioned more efficiently. Therefore, fatty acids, which the ω3 position is made unsaturated, can be produced efficiently.

In the above-mentioned method for producing fatty acid, α-linolenic acid (ALA), stearidonic acid, $20:4\Delta^{8,11,14,17}$ or eicosapentaenoic acid (EPA) are preferred as the fatty acid described above.

Food or the industrial products according to the present invention is characterized by including α-linolenic acid (ALA), stearidonic acid, $20-4\Delta^{8,11,14,17}$ or eicosapentaenoic acid (EPA) obtained by the above-mentioned method for producing fatty acid.

According to the above-mentioned constitution, since n-3 series fatty acid has a function suppressing allergy, inflammation, blood coagulation or vascular constriction, it can be utilized as food or industrial products.

The method for obtaining the polynucleotide having the ω3 fatty acid desaturation activity according to the present invention is characterized by comprising a step for obtaining a polynucleotide coding for a polypeptide having a ω3 fatty acid desaturation activity by (g) hybridization using a polynucleotide, which hybridizes to the above-mentioned polynucleotide under stringent conditions, or an oligonucleotide, which is a fragment of it, as a probe; or (h) PCR using a oligonucleotide, which is a fragment of the above-mentioned polynucleotide as a primer, from genomic DNA or cDNA prepared from organism.

According to the above-mentioned constitution, a polynucleotide coding for the polypeptide having ω3 fatty acid desaturation activity can be efficiently obtained.

Moreover, the polynucleotide according to the present invention may be a polynucleotide, which hybridizes to either of the above-mentioned (c), (d), (e) or (f) under stringent conditions.

According to the above-mentioned constitution, using the above polynucleotide as an antisense polynucleotide, expression of the polypeptide having ω3 fatty acid desaturation activity in the above-mentioned organisms, or the tissues or the cell therefrom can be controlled. Meanwhile, RNAi is caused if expressing the polynucleotide coding for the polypeptide of above-mentioned (a) or (b) and the polynucleotide of above-mentioned (c) through (f) at the same time within the same cell. Therefore, controlling the expression of the polypeptide becomes possible.

Moreover, the polynucleotide according to the present invention may be a fragment of the above-mentioned polynucleotide.

According to the above-mentioned constitution, the oligonucleotide mentioned above can be used as a hybridization probe for detecting a polynucleotide coding for the polypeptide, which has ω3 fatty acid desaturation activity or a primer to amplify the polynucleotide. Further, using the above-mentioned oligonucleotide, organisms or, tissues or cells therefrom, wherein the polypeptide having ω3 fatty acid desaturation activity is expressed, can be identified. Furthermore, using the above-mentioned oligonucleotide as an antisense oligonucleotide, the expression of the polypeptide havingω3 fatty acid desaturation activity in the organisms or, tissues or cells therefrom can be controlled.

The detection device according to the present invention is characterized in the fact, wherein a polynucleotide that hybridizes to either of the above-mentioned polynucleotide described in (c), (d), (e) or (f) under stringent conditions and/or the above-mentioned oligonucleotide that is a fragment of the nucleotide is fixed on the substrate.

According to the above-mentioned constitution, organisms, which express the polypeptide having ω3 fatty acid desaturation activity can easily be detected by detecting such polynucleotide or a polynucleotide that hybridizes to such oligonucleotide.

Further, the detection device according to the present invention may be the one, wherein the above-mentioned polypeptide is fixed on the substrate.

According to the above-mentioned constitution, the material that regulates ω3 fatty acid desaturation activity of the above-mentioned polypeptide can be easily detected by detecting the material interacting with the above-mentioned polypeptide.

Further, the detection device according to the present invention may be the one that the above-mentioned antibody is fixed on the substrate.

According to the above-mentioned constitution, the polypeptide having ω3 fatty acid desaturation activity can easily be detected by detecting the antigen bound to the above-mentioned antibody In addition, the present invention also includes a polypeptide having ω3 fatty acid desaturation activity, and having an amino acid sequence, wherein homology to the amino acid sequence represented by SEQ ID NO: 1 is 70% or more, and a polypeptide having ω3 fatty acid desaturation activity, and having an amino acid sequence, wherein the homology to the amino acid sequence represented by SEQ ID NO: 1 is 90% or more.

Since the polypeptide according to the present invention can catalyze the reaction, which makes intrinsic fatty acid in organisms such as fungi (yeasts, filamentous fungi, etc.) or plants unsaturated at the ω3 position, using the transformant, in which the recombinant expression vector containing polynucleotide coding for the polypeptide of the present invention is introduced, mass production of n-3 series fatty acid such as α-linolenic acid (ALA), stearidonic acid, $20{:}4\Delta^{8,11,14,17}$, eicosapentaenoic acids (EPA), etc., can be performed at low cost and with reduced environmental load. Further, by mass production of n-3 series fatty acid such as α-linolenic acid (ALA), stearidonic acid, $20{:}4\Delta^{8,11,14,17}$, eicosapentaenoic acids (EPA), etc., low cost food or industrial products can be provided.

BRIEF DESCRIPTION OF DRAWINGS

FIG. 1 represents deduced amino acid sequences of $\Delta^{12}$ fatty acid desaturase derived from *Mortierella alpine* and *Saccharomyces kluyveri*, and ω3 fatty acid desaturase derived from *Saccharomyces kluyveri*, and amino acid sequences of high homology among these.

FIG. 2 shows comparison of the amino acid sequence of ω3 fatty acid desaturase derived from *Mortierella alpina* with that of $\Delta^{12}$ fatty acid desaturase derived from *Mortierella alpina*, ω3 fatty acid desaturase derived from *Saccharomyces kluyveri*, ω3 fatty acid desaturase localized in endoplasmic reticulum of soybean and ω3 fatty acid desaturase localized in chloroplast of soybean.

FIG. 7 represents major PUFAs, which belong to n-3 and n-6 series, in animals.

BEST MODE FOR CARRYING OUT THE INVENTION

Figure 3:
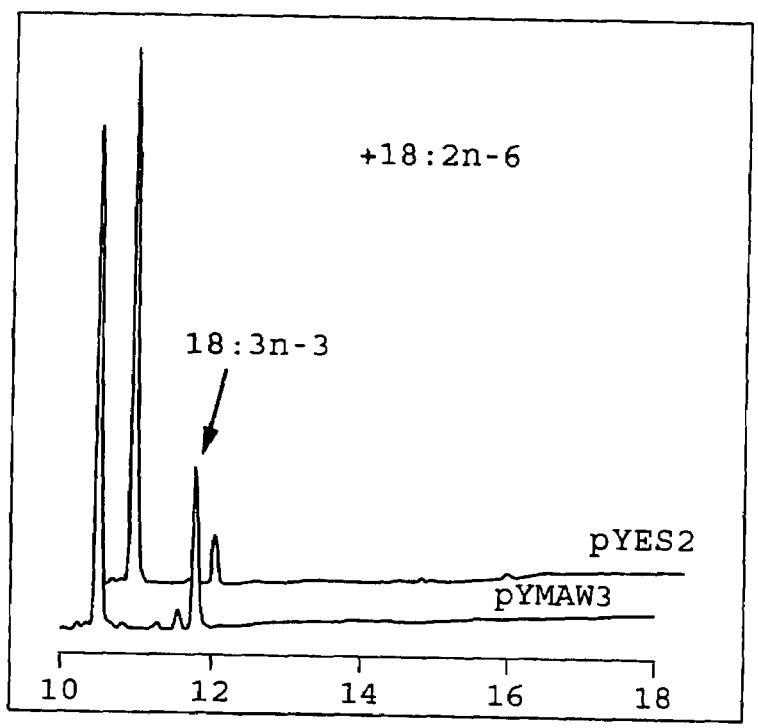
FIG. 3 shows a result of fatty acid analysis by gas chromatography in yeast *Saccharomyces cerevisiae*, in which pYMAW3 was introduced, in the case where linoleic acid was added as a substrate.

Hereinafter, the polypeptide according to the present invention, which has ω3 desaturation activity, the polynucleotide coding for the same and use thereof, are described in detail.

(1) Polypeptide

The polypeptide according to the present invention is a novel ω3 fatty acid desaturase, and makes ω3 position of fatty acid unsaturated to generate n-3 series fatty acid. The polypeptide according to the present invention is not limited as long as it has an activity that makes ω3 position of fatty acid unsaturated. However, as a substrate for ω3 fatty acid desaturation activity, preferred is a substance having desaturation activity at ω3 position of fatty acid, which has 18 and/or 20 carbons. Further, more preferred is a substance having desaturation activity at ω3 position of fatty acid, which has 18 and 20 carbons. Because a wide range of substrates to be desaturated at ω3 position can be used, various n-3 series fatty acid can be produced.

Fatty acid to be a substrate may be either saturated fatty acid or unsaturated fatty acid. However, more preferred is unsaturated fatty acid, and n-6 series fatty acid is further preferred. By making the ω3 position of n-6 series fatty acid unsaturated, PUFAs, which plays an important role in organism, can be produced.

Moreover, for the polypeptide of the present invention, preferred is a polypeptide having an activity that makes the ω3 position of n-6 series fatty acid as a substrate fatty acid unsaturated. However, number or position of double bond is not limited as long as such fatty acid is one having unsaturated bond at n-6 position. Among them, for the polypeptide according to the present invention, a polypeptide having an activity that makes the ω3 position of linoleic acid, γ-linolenic acid, dihomo-γ-linolenic acid, and arachidonic acid unsaturated, is particularly preferred. As a result, it is considered that by making the ω3 position unsaturated, synthesis from linoleic acid to α-linolenic acid, synthesis from γ-linolenic acid to stearidonic acid, synthesis from dihomo-γ-linolenic acid to $20{:}4\Delta^{8,11,14,17}$, and synthesis from arachidonic acid to eicosapentaenoic acid can be performed. The obtained n-3 series PUFAs can be efficiently utilized as food or industrial products because it has the function that suppresses allergy, inflammation, blood coagulation or vascular constriction.

In the specification, the term "polypeptide" can be used exchangeably for "peptide" or "protein". Moreover, the "fragment" of the polypeptide intends to a partial fragment of the polypeptide. The polypeptide according to the present invention may also be isolated from natural sources or chemically synthesized.

The term "isolated" polypeptide or protein intends to a polypeptide or a protein taken out from its natural environment. It is considered that a polypeptide and a protein, which is expressed in the host cell and produced recombinantly, is isolated the same as natural or recombinant polypeptide and protein, which are substantially purified by any appropriate techniques.

The polypeptide according to the present invention includes a natural purified product, a product produced by chemical synthesis protocol, and a product produced by recombinant techniques from prokaryotic or eukaryotic host (e.g., including bacteria, fungi (yeasts, filamentous fungi, etc.), higher plant cell, insect cell and mammalian cell). Depending on the host used in recombinant production protocol, the polypeptide of the present invention may be either glycosylated or non-glycosylated. Further, the polypeptide of the present invention may also include, in some cases, as a result of host-mediated process, a modified initial methionine residue.

The present invention provides a polypeptide having ω3 fatty acid desaturation activity. In one embodiment, the polypeptide of the present invention is a polypeptide consisting of the amino acid sequence represented by SEQ ID NO: 1, or a variant of the polypeptide consisting of the amino acid sequence represented by SEQ ID NO: 1, and a polypeptide having ω3 fatty acid desaturation activity.

The variant includes one containing deletion, insertion, reversion, repetition and substitution. Especially, "neutral" amino acid substitution in the polypeptide generally hardly influence on the activity of the polypeptide.

It is well known in the art that some amino acid residue in the amino acid sequence of polypeptide can easily be modified without affecting structure or function of the polypeptide significantly. In addition, it is also well known that in natural protein, not artificially modification, variant, which does not affect structure or function of the protein, is also present.

The persons skilled in the art can easily mutate one or plural amino acids in the amino acid sequence of the polypeptide by using a well-known techniques. For example, according to publicly known point mutagenesis, an arbitrary base of polynucleotide coding for the polypeptide can be mutated. Moreover, the deletion mutant or the addition mutant can be prepared by designing the primer corresponding to an arbitrary part of polynucleotide coding for the polypeptide. In addition, using the method described in the present specification, it can be easily determined whether the mutant prepared has the desired activity.

The variant of the present invention is not limited. However, preferred is a variant that does not affect an activity of the polypeptide according to the present invention. Specifically, example of the variant includes silent mutation, conservative substitution, and the like.

Typical conservative substitution includes substitution of one amino acid to another amino acid in aliphatic amino acids, Ala, Val, Leu and Ile; exchange of hydroxyl residues Ser and Thr; exchange of acidic residues Asp and Glu; exchange of amide residues Asn and Gln; exchange of basic residues Lys and Arg; and exchange of aromatic residues Phe and Tyr. In addition, silent substitution is a variant with no effect on activity of the polypeptide when the amino acid is substituted, added or deleted.

As shown above in detail, a further guidance about which change of amino acid seems to be phenotypically silent (that is, whether the change does not seem to have a significantly harmful effect on function) can be found in Bowie, J. U. et al., "Deciphering the Message in Protein Sequences: Tolerance to Amino Acid Substitutions", Science 247: 1306-1310 (1990), which is incorporated by reference in the specification.

For the polypeptide according to the embodiment, preferred is a polypeptide having a ω3 fatty acid desaturation activity, and consisting of
(a) the amino acid sequence represented by SEQ ID NO: 1; or
(b) an amino acid sequence, wherein one or plural amino acids are substituted, deleted, inserted or added in the amino acid sequence represented by SEQ ID NO: 1.

Above-mentioned "one or plural amino acids are substituted, deleted, inserted or added" means the fact that numeral range (preferably 10 or less, more preferably 7 or less, most preferably 5 or less) of amino acid enable to substitute, delete, insert or add by publicly known method for preparing a variant polypeptide such as site-specific mutagenesis is substituted, deleted, inserted or added. As described above, such a variant polypeptide is not limited to a polypeptide having mutation artificially introduced by publicly known method for preparing a variant polypeptide, but may be one, which is isolated and purified from naturally occurring polypeptide.

The present invention also encompasses a polypeptide having the amino acid sequence, wherein the homology to the amino acid sequence represented by SEQ ID NO: 1 is 70% or more, preferably 90% or more and possessing ω3 fatty acid desaturation activity. For the homology of amino acid sequence in such polypeptide, 70% or more is well, 90% or more is preferable, 95% or more is more preferable, 98% or more is more preferable, and 99% or more is particularly preferable.

Above-mentioned "homology" in the specification means the value obtained by the BLAST search (Basic local alignment search tool; Altschul, S. F. et al, J. Mol. Biol., 215, 403-410, 1990), and the homology of amino acid sequence can be determined according to the BLAST search algorithm. Specifically, using bl2seq program (Tatiana A. Tatusova and Thomas L. Madden, FEMS Microbiol. Lett. 174, 247-250, 1999) of the BLAST package (the sgi32 bit version, ver. 2.0.12; obtained from NCBI), the homology can be calculated according to the default parameter. As pairwise alignment parameter, program name for "blastp", Gap insertion Cost value for "0" and Gap extension Cost value for "0" are used, respectively. Also, "SEG" as a filter of the Query sequence, and "BLOSUM62" as Matrix are used.

The polypeptide of the present invention may be, but is not limited to, a polypeptide, wherein amino acid is bound by peptide bond. It may also be a complex polypeptide including the structures other than polypeptide. As "structures other than polypeptide", it includes, but is not especially limited to, when used in the specification, sugar chain and isoprenoid radical, etc.

In addition, the polypeptide of the present invention may be the one including an additional polypeptide. For example, the epitope labeled polypeptides such as His, Myc, and Flag are exemplified as an additional polypeptide.

In another embodiment, the polypeptide of the present invention can be recombinantly expressed in the modified form such as fusion protein. For example, to improve stability and sustention during purification step, the following operation or storage, additional amino acid in the polypeptide of the present invention, particularly the region of charged amino acid can be added to the N-terminus of the polypeptide.

For the polypeptide according to the embodiment, the tag label (tag sequence or marker sequence), which is the sequence coding for peptide that facilitates the purification of the fused polypeptide, may be added to the N-terminus or the C-terminus. Such a sequence can be removed before the final preparation of the polypeptide. In a specific, preferable embodiment of this aspect of the present invention, the tag amino acid sequence is a hexa-histidine peptide (for example, tag provided in the pQE vector (Qiagen, Inc.)), and many of them can be obtained publicly and/or commercially among the other. As described in, for example, Gentz et al., Proc. Natl. Acad. Sci. USA, 86: 821-824 (1989), which is incorporated by reference in the specification, hexa-histidine provides a convenient purification of fusion protein. "HA" tag is another useful peptide for the purification, which is corresponding to the epitope derived from influenza hemagglutinin (HA) protein, and it has been described by Wilson et al., Cell 37:767(1984), which is incorporated by reference in the specification. Such other fusion proteins include the polypeptide of the embodiment fused in Fc at the N-terminus or the C-terminus, or a fragment thereof.

In addition, the polypeptide of the present invention may be the one, wherein the polynucleotide of the present invention described below (a gene coding for the polypeptide of the present invention) is introduced into the host cell, and moreover, the polypeptide is expressed in the cell, or the one, which is isolated and purified from cells or tissues. Further, the polypeptide of the present invention may be the one that was chemically synthesized.

The recombinant production can be performed using a well-known method in a relevant field, e.g., using the vector and the cells as described below in detail.

Synthetic peptide can be synthesized by using publicly known method of chemical synthesis. For example, the method by Houghten, R. A., Proc. Natl. Acad. Sci. USA, 82: 5131-5135 (1985), which is incorporated by reference in the specification, can be used. In addition, this "Simultaneous Multiple Peptide Synthesis (SNPS)" process is described in the U.S. Pat. No. 4,631,211 of Houghten et al. (1986). In this procedure, an individual resin for the solid phase synthesis of various peptide, which is contained in a separate solvent penetration packet, enables the best use of a lot of same repetition processes relating to the solid phase synthesis. A complete manual procedure enables 500-1000 or more to be synthesized at the same time (Houghten, cited above, 5134). These documents are incorporated by reference in the specification.

As described below in detail, the polypeptide according to the present invention is useful for the method and the kit for generating n-3 series fatty acid that makes ω3 position of fatty acid unsaturated.

Thus, it can be said that the polypeptide of the present invention only has to contain at least the amino acid sequence represented by SEQ ID NO: 1. That is, it is necessary to note that the polypeptide that consists of the amino acid sequence represented by SEQ ID NO: 1 and an arbitrary amino acid sequence having a specific function (for example, tag) is also included in this invention. Moreover, the amino acid sequence represented by SEQ ID NO: 1 and an arbitrary amino acid sequence may be ligated by appropriate linker peptide so as not to inhibit each function.

(2) Polynucleotide

The present invention provides a polynucleotide coding for the polypeptide of the present invention that has ω3 fatty acid desaturation activity. The term "polynucleotide" can be used interchangeably for "nucleic acid" or "nucleic acid molecule", when used in the specification, and is intended to a polymer of nucleotide. The term "base sequence" can be used interchangeably for "nucleic acid sequence" or "nucleotide sequence", and is shown as sequence of deoxyribonucleotide (abbreviated as A, G, C, and T) when used in the specification. Moreover, "the polynucleotide comprising the base sequence represented by SEQ ID NO: 2, or a fragment thereof" is intended to a polynucleotide comprising a sequence shown by respective deoxynucleotides, A, G, C and T in SEQ ID NO: 2, or a fragment portion thereof.

The polynucleotide according to the present invention can exist in the form of RNA (for example, mRNA), or in the form of DNA (for example, cDNA or genomic DNA). DNA may be either double stranded or single stranded. A single stranded DNA or RNA may be coding strand (also known as sense strand), or may be non-coding strand (also known as antisense strand).

When used in the specification, the term "oligonucleotide" means a substance, in which several to tens of nucleotides are bound, and can be used interchangeably for "polynucleotide". Short oligonucleotide is called like, for example, dinucleotide (dimer) and trinucleotide (trimer), and the long one is shown by the number of nucleotides polymerized like 30mer or 100mer, etc. Oligonucleotide may be generated as a fragment of longer polynucleotide, and may be chemically synthesized.

For fragment of the polynucleotide of the present invention, preferred length may be appropriately selected depending on use of PCR or probe. At least 12 nt (nucleotides) is preferable, and at least 15 nt or more is more preferable. More preferable is within the range of 15-25 nt, and the length may be 30 nt or more, and alternatively, 40 nt or more, but it is not particularly limited. For example, by the fragment including the length of at least 20 nt, the fragment comprising 20 or more contiguous base from the base sequence represented by SEQ ID NO: 2 or SEQ ID NO: 3 is intended. Since the base sequence represented by SEQ ID NO: 2 or SEQ ID NO: 3 is provided if the specification is referred, the persons skilled in the art can easily prepare DNA fragment based on SEQ ID NO: 2 or SEQ ID NO: 3. For example, cleavage by the restriction endonuclease or the shearing by ultrasonication can be easily used to prepare various size of fragment. Alternatively, such a fragment can be prepared synthetically. An appropriate fragment (oligonucleotide) is synthesized with 392 synthesizer by Applied Biosystems Incorporated (ABI, 850 Lincoln Center Dr., Foster City, Calif. 94404).

The polynucleotide according to the present invention can be fused to the polynucleotide coding for the above-mentioned tag label (tag sequence or marker sequence) on the 5' or 3' sides.

The present invention further relates to the variant of the polynucleotide coding for the polypeptide that has ω3 fatty acid desaturation activity. The variant can be naturally generated like the allelic mutant of nature. By "allelic mutant", one of the interchangeable forms of genes that occupy a given gene loci on the chromosome of the organism is intended. The variant, which does not exist naturally, can be generated using a well-known method for mutagenesis.

Such a variant includes a variant, wherein one or plural bases are deleted, substituted or added, in the base sequence of polynucleotide coding for the polypeptide that has ω3 fatty acid desaturation activity. The variant can be mutated in coding region or non-coding region, or both. The mutation in the coding region can generate deletion, substitution or addition of the amino acid, which is conservative or non-conservative.

The present invention further provides an isolated polynucleotide comprising a polynucleotide coding for the polypeptide that has ω3 fatty acid desaturation activity or a polynucleotide that hybridizes to the polynucleotide under stringent hybridization conditions In one embodiment, the polynucleotide according to the present invention is a polynucleotide coding for a polypeptide having a ω3 fatty acid desaturation activity, and preferably either (a) or (b) described below:

(a) a polynucleotide coding for a polypeptide consisting of the amino acid sequence represented by SEQ ID NO: 1; or
(b) a polynucleotide coding for a polypeptide consisting of an amino acid sequence, wherein one or plural amino acids are substituted, deleted, inserted or added in the amino acid sequence represented by SEQ ID NO: 1.

In another embodiment, the polynucleotide of the present invention is a polynucleotide coding for a polypeptide having a ω3 fatty acid desaturation activity, and preferably any of (c), (d), (e) or (f) described below:

(c) a polynucleotide consisting of the base sequence represented by SEQ ID NO: 2 or SEQ ID NO: 3;
(d) a polynucleotide consisting of the base sequence from 14 to 1366 of the base sequence represented by SEQ ID NO: 2;
(e) a polynucleotide, which hybridizes with a polynucleotide consisting of a complementary base sequence to the base sequence represented by SEQ ID NO: 2 or SEQ ID NO: 3 under stringent conditions;
(f) a polynucleotide, which hybridizes with a polynucleotide consisting of a complementary base sequence to the base sequence from 14 to 1366 of the base sequence represented by SEQ ID NO: 2.

In addition, the above-mentioned "stringent conditions" means that hybridization occurs only when at least 90% or more, preferably at least 95% or more, most preferably 97% identity is present between sequences.

The above-mentioned hybridization can be performed by the well-known method such as the method described in Sambrook et al., Molecular Cloning, A Laboratory Manual, 2nd Ed., Cold Spring Harbor Laboratory (1989). In general, since the stringency becomes high when the temperature is higher and the concentration of salts is lower, that is, it becomes to be difficult to hybridize, a polynucleotide, which is more homologous, can be obtained. For the conditions of hybridization, publicly known conditions can be used preferably and is not particularly limited. For example, the conditions comprising 42° C., 6×SSPE, 50% formamide, 1% SDS, 100 μg/ml salmon sperm DNA, 5× Denhardt's solution, wherein 1×SSPE: 0.18 M sodium chloride, 10 mM sodium phosphate, pH7.7, 1 mM EDTA; 5× Denhardt's solution: 0.1% bovine serum albumin, 0.1% Ficoll, 0.1% polyvinylpyrrolidone, is used.

Further in another embodiment, the polynucleotide according to the present invention is preferably a polynucleotide that hybridizes to either of polynucleotide of above-mentioned (c) (d), (e) or (f).

In another embodiment, it is preferable for the polynucleotide of the present invention to be the oligonucleotide, which is a fragment of the above-mentioned polynucleotide.

The polynucleotide or the oligonucleotide according to the present invention includes not only double stranded DNA, also single stranded DNA such as sense strand and antisense strand that constitute double stranded DNA and RNA. The polynucleotide or the oligonucleotide according to the present invention can be utilized as a tool for manipulation of gene expression by antisense RNA mechanism.

Antisense RNA technology makes a basic principle introduction of the chimeric gene, which generates a complementary RNA transcript to a target gene. The phenotype, which is obtained as the result is reduction of the gene product derived from an endogenous gene. By introducing the polynucleotide or the oligonucleotide according to the present invention, contents of the polypeptide having ω3 fatty acid desaturation activity are reduced and contents of n-3 series fatty acid in the organism can be reduced. Moreover, it becomes possible to prevent reduction of the content of fatty acid, which serves as a substrate, simultaneously.

Thus when, for example, production of n-6 series fatty acid such as arachidonic acid is desired, by reducing amount of the polypeptide having ω3 fatty acid desaturation activity, reduction of amount of arachidonic acid by ω3 desaturation can be prevented. DNA includes cDNA or genomic DNA, etc, which is obtained by, for example, cloning, techniques for chemically synthesis, or a combination thereof Furthermore, the polynucleotide or the oligonucleotide according to the present invention may be the one that includes sequence of untranslation region (UTR), sequence from vector, which comprises a sequence from expression vector, and the like.

Moreover, it is also possible to suppress expression of polypeptide by RNA interference (RNAi). RNAi is phenomenon, wherein gene expression is suppressed by introducing the double stranded RNA into a cell, and degrading mRNA homologous to the double stranded RNA in a cell. Using this method, the amount of polypeptide that has ω3 fatty acid desaturation activity can be reduced. As a result, the contents of n-3 series fatty acid in organism can be reduced. Moreover, it becomes possible to prevent reduction of the amount of the fatty acid, which serves as a substrate, simultaneously. Specifically, RNAi is caused if expressing the polynucleotide coding for the polypeptide of above-mentioned (a) or (b) and the polynucleotide of above-mentioned (c) through (f) at the same time within the same cell. Therefore, controlling the expression of the polypeptide becomes possible.

The method for obtaining the polynucleotide or the oligonucleotide according to the present invention includes a method, wherein DNA fragment comprising the polynucleotide or the oligonucleotide according to the present invention is isolated and cloned by publicly known techniques. For example, after preparing a probe that specifically hybridizes to a portion of the base sequence of the polynucleotide of the present invention, genomic DNA library or cDNA library may be screened. For such a probe, any sequence and/or any length is usable as long as it is the probe, which specifically hybridizes to the base sequence of the polynucleotide of the present invention or a portion of its complementary sequence.

Alternatively, for the method for obtaining the polynucleotide or the oligonucleotide according to the present invention, the method using amplification means such as PCR is included. For example, each primer is prepared from 5' and 3' sequences or their complementary sequences among cDNA (s) for the polynucleotide in the present invention. Then using these primers and genomic DNA as a template, PCR is performed. By amplifying DNA region between the primers, DNA fragment containing the polynucleotide of the present invention can be acquired in large quantities.

Preferably, the source for obtaining the polypeptide of the present invention includes, but is not especially limited to, a biological material including the ω3 unsaturated fatty acid in addition of fatty acid of 18 and 20 carbons having unsaturated bond at n-6 position. When used in the specification, the term "biological material" means a biological sample, that is, the tissue sample or cell sample obtained from organisms. Since, it is considered that, for example, α-linolenic acid, stearidonic acid, $20:4\Delta^{8,11,14,17}$, and eicosapentaenoic acid is generated by ω3 desaturation reaction from linoleic acid, γ-linolenic acid, dihomo-γ-linolenic acid and arachidonic acid, respectively, the polynucleotide coding for the polypeptide catalyzing synthesis reaction of n-3 series fatty acid can be obtained as long as the biological material comprises, for example, all or a portion of the substrate-product pair. In Examples mentioned later, *Mortierella alpina* is used as the above-mentioned source, but it is not limited to this.

In addition, the present invention intends to provide the polynucleotide coding for the polypeptide which has the activity which makes the ω3 position of fatty acid having 18 and/or 20 carbons unsaturated, and the oligonucleotide which hybridizes to the polynucleotide, and the purpose does not exist in a method for preparing the polynucleotide and the oligonucleotide specifically described in the specification. Therefore, it should be noted that the polynucleotide coding for the polypeptide having the activity, which makes the ω3 position of fatty acid having 18 and/or 20 carbons unsaturated, obtained by a method other than that described above also belongs to the technical scope of the present invention.

(3) Antibody

The present invention provides an antibody specifically bound to the polypeptide having ω3 fatty acid desaturation activity. When used in this specification, the term "antibody" means an immunoglobulin (IgA, IgD, IgE, IgG, IgM(s) and such Fab fragment, F(ab')$_2$ fragment, Fc fragment), and includes, but is not limited to, a polyclonal antibody, a monoclonal antibody, a single chain antibody, an anti-idiotype antibody, and a humanized antibody. The antibody according to the present invention may be useful for choosing the biological material, which expresses the polypeptide having ω3 fatty acid desaturation activity.

An "antibody" can be prepared according to various publicly known methods (for example, Harlow et al., "Antibodies: A laboratory manual, Cold Spring Harbor Laboratory, New York (1988)", Iwasaki et al., "monoclonal antibody: hybridoma and ELISA, Kodansha (1991)").

A peptide antibody is prepared by the well-known method in the art. For example, see Chow, M. et al., Proc. Natl. Acad. Sci. USA 82: 910-914 and Bittle, F. J. et al., J. Gen. Virol. 66: 2347-2354 (1985), which are incorporated by references in the specification. Generally, an animal may be immunized with isolated peptide. However, the additional immunity of the anti-peptide titer may be carried out by carrying out coupling of the peptide to a macromolecule career (for example, keyhole limpet hemocyanin (KLH) or tetanus toxoid). For example, coupling of the peptide containing cysteine may be carried out to a career using linker such as m-maleimidebenzoyl-N-hydroxysuccinimide ester (MBS), and, on the other hand, coupling of other peptide may be carried out to a career using a more general linking agent such as glutaraldehyde. Animals such as rabbits, rats and mice are immunized with either free peptide or carrier-coupling peptide by interperitoneal and/or intradermal injection of, for example, about 100 µg of peptide or emulsion comprising carrier protein, and Freund's adjuvant. Several additional immunity injection may be necessitated every about two weeks in order to provide anti-peptide antibody having an useful titer detectable by ELISA assay using free peptide adsorbed on the solid surface. The titer of the anti-peptide antibody in serum from immunized animals can be increased by selection of the anti-peptide antibody, for example, by adsorption to the peptide on the solid support and elution of the selected antibody by the well-known method in the art.

When used in the specification, the term "the antibody specifically bound to the polypeptide having ω3 fatty acid desaturation activity" means the fact that the complete antibody molecule and antibody fragment (for example, Fab and F(ab')$_2$ fragment), which can specifically bind to the polypeptide antigen having ω3 fatty acid desaturation activity are included. Fab and F(ab')$_2$ fragment lack Fc portion of a complete antibody, and are removed still more quickly by circulation, and cannot hardly have nonspecific tissue binding of a complete antibody (Wahl et al., J. Nucl. Med., 24: 316-325 (1983), which is incorporated by reference in the specification. Therefore, such fragment is preferable.

Furthermore, an additional antibody that can bind to the peptide antigen of the polypeptide having ω3 fatty acid desaturase activity can be produced by two-step procedure via use of anti-idiotype antibody. By such a method, using the fact that antibody itself is an antigen, as a result, an antibody bound to secondary antibody can be obtained. According to this method, the antibody specifically bound to the polypeptide having ω3 fatty acid desaturase activity is used in order to immunize the animal, preferably mouse. Subsequently, splenocytes of such an animal is used for the production of hybridoma cells. Then the hybridoma cells are screened for identifying clones that produces antibody, wherein the ability to bind to the antibody that is bound specifically to the polypeptide having ω3 fatty acid desaturase activity can be inhibited by polypeptide antigen having ω3 fatty acid desaturase activity. Since such an antibody includes the anti-idiotype antibody to the antibody specifically bound to the polypeptide that has ω3 fatty acid desaturase activity, it can be used to immunize an animal for induction of formation of an additional antibody specifically bound to the polypeptide having ω3 fatty acid desaturase activity.

It is clear that Fab, F(ab')$_2$, and other fragment of the antibody according to the present invention can be used according to the method disclosed in the specification. Such a fragment is typically produced according to cleavage by the proteolysis using the enzyme such as papain, wherein the Fab fragment is caused, or pepsins, wherein the F(ab')$_2$ fragment is caused. Alternatively, the polypeptide binding fragment that has the ω3 fatty acid desaturation activity can be produced by applying recombinant DNA techniques or by synthetic chemistry.

Thus, it can be said that the antibody of the present invention may provide at least with the antibody fragment (for example, Fab and F(ab')$_2$ fragment) that recognizes the polypeptide having ω3 fatty acid desaturation activity of the present invention. That is, it should be noted that the immunoglobulin consisting of the antibody fragment that recognizes the polypeptide having ω3 fatty acid desaturation activity of the present invention and the Fc fragment of different antibody molecules is also included.

In a word, the present invention intends to provide the antibody that recognizes the polypeptide having ω3 fatty acid desaturation activity according to the present invention, and the purpose does not exist in the kind of the individual immunoglobulin (IgA, IgD, IgE, IgG or IgM), the method for preparing the chimera antibody, the method for preparing the peptide antigen, etc., which are specifically described in the specification. Therefore, it should be noted that the antibody acquired by a method other than that described above also belongs within the technical scope of the present invention.

(4) Use of the Polypeptide and/or the Polynucleotide According to the present Invention (4-1) Vector The present invention provides a vector used for generating the polypeptide having ω3 fatty acid desaturation activity. The vector may be either a vector used for the in vitro translation or a vector used for recombinant expression.

The vector of the present invention is not particularly limited as long as the one including the above-mentioned polynucleotide of the present invention. For example, included is the recombinant expression vector, wherein cDNA of polynucleotide coding for the polypeptide having ω3 fatty acid desaturation activity is inserted. For the method for preparing a recombinant expression vector, a method using plasmid, phage or cosmid is included, but is not particularly limited.

A specific kind of the vector is not limited particularly, and the vector able to express in the host cell may be appropriately selected. That is, to absolutely express the polynucleotide of the present invention depending on the kind of host cell, a promoter sequence is appropriately selected, and the promoter sequence and the vector, wherein the polynucleotide of the present invention is integrated into various plasmid, etc., may be utilized as an expression vector.

The expression vector preferably comprises at least one selection marker. For the marker, antibiotics resistance gene, a marker gene that complements auxotrophic strain, i.e., auxotrophic marker, etc. can be used. Specifically, for example, for eukaryotic cell culture, dihydrofolate reductase or neomycin resistance is included. For the culture of Escherichia coli and other bacteria, tetracycline resistance gene or ampicirin resistance gene is included. However, these are not especially limited.

It can be confirmed whether the polynucleotide of the present invention was introduced into the host cell using the above-mentioned selection marker. Alternatively, the polypeptide of the present invention may be expressed as a fused polypeptide. For example, using Green Fluorescent Protein (GFP) derived from *Aequorea coerulescens* as a marker, the polypeptide of the present invention may be expressed as GFP-fused polypeptide. As a result, introduction and expression of the gene can be confirmed.

Moreover, when the recombinant expression vector is used to transform the plant, the vector is not particularly limited as long as it is a vector that is able to make the polynucleotide of the present invention expressed in the plant. For such a vector, included is for example, a vector having the promoter that constitutively makes polynucleotide expressed in plant cells (e.g., 35S promoter of cauliflower mosaic virus) or a vector having the promoter that is inductively activated by exogenous stimuli.

Thus, it can be said that the vector according to the present invention may comprise at least polynucleotide coding for the polypeptide of the present invention. That is, it should be noted that vectors other than the expression vector is included within the technical scope of the present invention.

In a word, the present invention intends to provide the vector comprising polynucleotide coding for the polypeptide of the present invention, and the purpose does not exist in an individual kind of vectors and organisms, a method for preparing a vector and introducing it into the cell, which are specifically described in the specification. Therefore, it should be noted that the vector acquired using a kind of vector and methods for preparing a vector other than that mentioned above also belongs within the technical scope of the present invention.

(4-2) Host and Transformation Method

The above-mentioned host is not particularly limited, and publicly known various organisms can preferably be used. Specifically, for example, bacteria such as *Escherichia coli* (*E. coli*); fungi such as yeasts (budding yeast *Saccharomyces cerevisiae* and fission yeast *Schzosaccharomyces pombe*) and filamentous fungi, etc.; *Caenorhabditis elegans* (*C. elegans*); oocyte of *Xenopus laevis*, mammals such as pigs, rats, and mice, etc. and other animals, etc. are included, but are not particularly limited. An appropriate culture medium and the condition for the above-mentioned host cell are well known in the art.

Moreover, the target plant for the transformation in the present invention means the entire plant body, the plant organ (for example, leaf, petal, stalk, root, and seed, etc.), the plant tissues (for example, epidermis, phloem, parenchyma, xylem, fibrovascular bundle, palisade tissue, and cancellous tissue, etc.) or the plant culture cells or the plant cells in various forms (for example, suspension cultured cells), protoplast and segment of the leaves, callus and the like. As the plant used for the transformation, it is not particularly limited, and either of the plant that belongs to the monocotyledon class or the dicotyledon class is acceptable.

The method for introducing the above-mentioned expression vector into the host cell, i.e., the transformation method is not particularly limited. Publicly known method such as electroporation, calcium phosphate method, liposome method, DEAE dextran method, acetic acid lithium method, and the particle delivery method, etc. can suitably be used. Moreover, when the polypeptide of the present invention is transferred into insect and expressed, the expression system using Baculovirus may be used.

A transformation method publicly known by the persons skilled in the art (for example, *Agrobacterium* method, gene gun, PEG method, and electroporation method, etc.) is used for the introduction of the gene into the plant. For example, the method using *Agrobacterium* and the method for directly introducing a gene into the plant cell are well known. When the *Agrobacterium* method is used, the transformed plant can be acquired by introducing the constructed expression vector for plants into an appropriate *Agrobacterium* such as *Agrobacterium tumefaciens*, and making the bacterium infect to leaf section aseptically cultured according to leaf disk method (written by Hirofumi Uchimiya, plant gene manipulation manual, 1990, 27-31 pp, Kodansha Scientific, Tokyo) etc.

Moreover, the method by Nagel et al. (Micribiol. Lett., 67, 325 (1990)) can also be used. This method is a method, wherein firstly the expression vector is introduced into *Agrobacterium*, and subsequently, the transformed *Agrobacterium* is introduced into the plant cell or the plant tissues by the method described in Plant Molecular Biology Manual (S. B. Gelvin et al., Academic Press Publishers). Herein, "plant tissues" includes callus obtained by culturing the plant cells. When transformation is performed using the *Agrobacterium* method, binary vector such as pBI121 or pPZP202 can be used.

Moreover, the electroporation method and the gene gun method are known as a method for directly introducing the gene into a plant cell or into a plant tissue. When the gene gun is used, plant body, plant organ, and plant tissue may be used as it is. Alternatively, the gene gun may be used after preparing segment or protoplast. The sample prepared like this can be processed with a gene introduction device (for example, PDS-1000/He (BIO-RAD) etc.). Depending on plant or sample, usually conditions for treatment are as follows: the pressure of about 450-2000 psi and the distance of about 4-12 cm The cell or the plant tissue, into which the gene is introduced, is firstly selected by drug resistance such as hygromycin resistance etc., and then, reproduced to the plant body according to the ordinary method. The plant body can be reproduced from the transformed cell depending on the kind of the plant cell by a method publicly known to the persons skilled in the art.

When the plant culture cell is used as a host, the transformation is performed to the cultured cell by introducing the recombinant vector using the gene gun or electroporation method and so on. Callus, shoot or capillary root obtained as a result of the transformation, can used to a cell culture, tissue culture or organ culture as it is. In addition, using plant tissue culture method historically known, it is possible to reproduce plant body by administering a suitable concentration of plant hormone (auxin, cytokinin, gibberellin, abscisic acid, ethylene, and brassinolide).

(4-3) Transformant

The present invention provides the transformant, into which the polynucleotide coding for the polypeptide that has ω3 fatty acid desaturation activity mentioned above is introduced. Herein, "transformant" means not only the cell, the tissue or the organ, but also the organism individual.

The method for preparing (producing) the transformant includes for example, but is not particularly limited to, the method of transformation by introducing the recombinant vector mentioned above into the host. Moreover, the target organisms for transformation includes, but is not especially limited to, various microorganisms, the plants or animals exemplified above as a host.

In the transformant according to the present invention, fatty acid composition is modified from naturally occurring fatty acid. The transformant according to the present invention is preferably fungi (yeasts, filamentous fungi, etc.), plant or progeny thereof, animals or, cells or tissues therefrom. For the plant, particularly preferred is soybean, rapeseed, sesame, olive, linseed, maize, sunflower or safflower. That is, the plant grown for an oil and fat manufacturing can be preferably used as a plant used for the transformation in the present invention.

The transformant comprising the polynucleotide coding for the polypeptide of the present invention can be obtained by introducing the recombinant vector comprising the polynucleotide into the plant so that the gene may express.

The confirmation of introduction of the gene can be performed by PCR method, Southern hybridization method, and Northern hybridization method, etc. For example, DNA is prepared from the transformant, DNA specific primers are designed, and PCR is performed. PCR can be done on the condition similar to that used to prepare the above-mentioned plasmid. The transformation can be confirmed by agarose gel electrophoresis, polyacrylamide gel electrophoresis or capillary electrophoresis for amplified products, etc., staining with ethidium bromide or SYBR Green solution, etc., and detecting the amplified product as one band. Moreover, the amplified products can be detected by PCR using primers previously labeled with fluorescent dye, etc. In addition, the method for confirming the amplified products by binding the products to solid phase such as a microplate and, fluorescence or enzyme reaction, can be also applied.

If the transformant, wherein the polynucleotide of the present invention was integrated into the genome is obtained once, the progeny can be obtained by sexual reproduction or asexual reproduction of the organism. Moreover, from the organisms or a progeny thereof, or clone thereof, when plant is used, the plant body can be mass-produced based on seed, fruit, icker, tuber, root tuber, stock, callus, protoplast, etc. Therefore, the present invention includes an organism, in which the polynucleotide of the present invention is expressively introduced, or a progeny thereof, which has the same characteristics as the organism, or tissues derived from the above.

Thus, it can be said that as for the transformant of the present invention, the polynucleotide coding for the polypeptide of the present invention may only have been introduced at least. That is, it should be noted that the transformant generated with means other than the recombinant expression vector is included within the technical scope of the present invention.

In a word, the present invention intends to provide the transformant characterized by introducing the polynucleotide coding for the polypeptide of the present invention, and does not exist in an individual kind of vector and the introduction method specifically described in the specification. Therefore, it should be noted that the transformant acquired by using kind of vector, organisms, methods for preparing a vector and introducing it to the cell other than that mentioned above also belongs within the technical scope of the present invention.

(4-4) Production Method of Polypeptide

The present invention provides a method for producing the polypeptides according to the present invention.

In one embodiment, the production method of the polypeptide according to the present invention is characterized by using the vector comprising the polynucleotide coding for the polypeptide of the present invention.

In one aspect of the embodiment, preferably the production method of the polypeptide of the embodiment is to apply the above-mentioned vector to the cell-free protein synthesis system. When the cell-free protein synthesis system is used, various kinds of commercially available kits may be utilized. Preferably, the production method of the polypeptide of the embodiment encompasses a step, wherein the above-mentioned vector and the cell-free protein synthesis solution are incubated.

In another aspect of the embodiment, preferably the production method of the polypeptide of the embodiment is to use the recombinant expression system. When the recombinant expression system is used, applied is a method, wherein after integration of the polynucleotide of the present invention into the recombinant expression vector, the vector is expressively introduced into the host by publicly known method and the above-mentioned polypeptide obtained by translation in the host is purified. The recombinant expression vector may be plasmid or others, and may only be able to introduce target polynucleotide into the host. Preferably, the production method of the polypeptide of the embodiment encompasses a step, in which the above-mentioned vector is introduced into the host.

As described above, when the exogenous polynucleotide is introduced into the host, preferably, in the expression vector, a promoter that functions to express the exogenous polypeptide in the host is integrated. The method for purifying the polypeptide recombinantly produced enables to purify the target polypeptide with comparative ease by using a tag, etc., depending on the host used or the character of the polypeptide.

Preferably, the production method of the polypeptide of the embodiment further includes the process of purifying the polypeptide from the extracts of cells or tissues comprising the polypeptide of the present invention. For the step for purifying the polypeptide, preferred is a step, wherein after preparing cell extracts from cells or tissues by well-known method, e.g., a method for recovering soluble fraction after disruption of cells or tissues and centrifugation, the polypeptide is purified from the cell extracts by well-known method such as precipitation by ammonium sulfate or ethanol, acid extraction, anion or cation exchange chromatography, phosphocellulose chromatography, hydrophobic interaction chromatography, affinity chromatography, hydroxylapatite chromatography and lectin chromatography, but is not limited to these. Most preferably, High performance liquid chromatography ("HPLC") is used for purification.

In another embodiment, the production method of the polypeptide according to the present invention is characterized by purifying the polypeptide from cells or tissues that naturally expresses the polypeptide of the present invention. Preferably, the production method of the polypeptide according to the embodiment encompasses a step identifying the cells or tissues that naturally expresses the polypeptide of the present invention using the antibody or the oligonucleotide described above. In addition, the production method of the polypeptide according to the embodiment further encompasses a step purifying the above-mentioned polypeptide.

Further in another embodiment, the production method of the polypeptide of the present invention is characterized by chemically synthesizing the polypeptide of the present invention. The persons skilled in the art will easily understand that if well-known chemical synthesis technology is applied based on the amino acid sequence of the polypeptide of the present invention described in the specification, the polypeptide of the present invention can be synthesized chemically.

As mentioned above, the polypeptide acquired by the production method of the polypeptides of the present inventions may be either a variant polypeptide that naturally occurs, or a variant polypeptide that is artificially prepared.

The method for preparing variant polypeptide is not especially limited. The variant polypeptide can be prepared by using well-known method for preparing variant polypeptide, for example, site-specific mutagenesis (see, e.g., Hashimoto-Gotoh, Gene 152: 271-275 (1995)), a method for preparing variant polypeptide by introducing point mutation into the base sequence with PCR method, or a method for preparing mutant strain by insertion of transposon, etc. For preparation of the variant polypeptide, commercially available kits may be utilized.

Thus, the production method of the polypeptide of the present invention may only use the publicly known and common use technology, at least based on the amino acid sequence of the polypeptide that has ω3 fatty acid desaturation activity or the base sequence of the polynucleotide coding for the polypeptide that has ω3 fatty acid desaturation activity.

In a word, the present invention intends to provide the production method of the polypeptide having ω3 fatty acid desaturation activity, and it should be noted that the production method including the processes other than various processes of the above-mentioned also belongs within the technical scope of the present invention.

(4-5) Production Method of Fatty Acids

This invention provides the production method of fatty acids by using organisms or cells that express the polypeptide of the present invention. The above-mentioned organism may be either a naturally occurring unmodified organism or a transformant using recombinant expression system.

In one embodiment, by the production method of fatty acids according to the present invention, fatty acids are produced using the organism transformed with polynucleotide coding for the polypeptide of the present invention or a tissue thereof Preferably, the above-mentioned organism is fungi (yeasts, filamentous fungi, etc.), plants or animals.

In a preferable aspect of the embodiment, the production method of fatty acid according to the present invention encompasses a step introducing the polynucleotide coding for the polypeptide of the present invention into the above-mentioned organism. For the step introducing the polynucleotide coding for the polypeptide of the present invention into the above-mentioned organism, various methods for introducing genes described above may be utilized. In the aspect of the embodiment, the content of fatty acid before or after transformation in the organism is different. Specifically, for fatty acid obtained from the organism, the contents of n-3 series fatty acid such as α-linolenic acid, stearidonic acid, $20:4\Delta^{8,11,14,17}$, and eicosapentaenoic acid are increased. Preferably, the production method of fatty acids according to the aspect of the embodiment further includes a step extracting fatty acids from the above-mentioned organism.

For example, oil comprising the fatty acid extracted from the transformant of the present invention, in which the contents of α-linolenic acid, stearidonic acid, $20:4\Delta^{8,11,14,17}$, and/or eicosapentaenoic acid are increased as described above, is provided as a food, wherein the contents of α-linolenic acid, stearidonic acid, $20:4\Delta^{8,11,14,17}$, and/or eicosapentaenoic acid are high. Moreover, when the transformed plant body is utilized, seed, fruit, icker, tuber, and/or root tuber, as well as fatty acids extracted, are also provided as a food comprising much of α-linolenic acid, stearidonic acid, $20:4\Delta^{8,11,14,17}$, and/or eicosapentaenoic acid. The object, in which the fatty acid composition is modified, is not particularly limited. Alternatively, other than plants, all organisms including animals, bacteria or fungi (yeast, filamentous fungi, etc.) may be targeted.

In another embodiment, the production method of fatty acids of the present invention includes a step introducing the polynucleotide or the oligonucleotide of the present invention as an antisense nucleotide into the organism that naturally expresses the polypeptide of the present invention. In the step introducing the polynucleotide or the oligonucleotide of the present invention into the organism, the antisense RNA technology described above may be utilized. In addition, the aforementioned RNAi technology can also be used.

Preferably, the production method of fatty acids of the embodiment further includes a step identifying the above-mentioned organism that naturally expresses the polypeptide of the present invention using the above-mentioned antibody or oligonucleotide. Preferably, the production method of fatty acids of the aspect of the embodiment further encompasses a step extracting fatty acids from the above-mentioned organism.

In the embodiment, the fatty acid composition is different before or after introducing the above-mentioned polynucleotide or oligonucleotide in the above-mentioned organism. Specifically, for fatty acid obtained from the organism, the contents of n-3 series fatty acid such as α-linolenic acid, stearidonic acid, $20:4\Delta^{8,11,14,17}$, and eicosapentaenoic acid that naturally produced are decreased. Moreover, the range of reduction of the contents for linoleic acid, γ-linolenic acid, dihomo-γ-linolenic acid, arachidonic acid, etc. becomes smaller.

Thus, the production method of the fatty acid of the present invention may use at least the organism expressing the polypeptide of the present invention.

In a word, the present invention intends to provide the production method of fatty acids based on the organism, to which the fatty acid composition is modified by the polypeptide of the present invention, and it should be noted that the production method that uses an animal, a plant or various microorganisms as the above-mentioned organism also belongs within the technical scope of the present invention.

(4-6) Food and Industrial Products

The present invention provides food and the industrial products manufactured using the fatty acid obtained by the production method of fatty acids described above. When the transformant is plant, the food described in the section may either seed, fruit, icker, tuber, and/or root tuber, or food produced using the fatty acid extracted from the above-mentioned transformant. Moreover, when the transformant mentioned above is a microorganism, it may be either the microorganism concerned, or the processed products such as extracts. In addition, the food of the present invention may either meat or milk of the animal that is the transformant mentioned above.

Moreover, for the industrial products, food additives or food additives for animal manufactured using fatty acid extracted from the above-mentioned transformant are included. As described above, since, for n-3 series PUFAs, many physiological activities commencing with antithrombotic action and improvement of serum lipid for EPA, and improvement of learning function and anticancer action for DHA are known, n-3 series PUFAs is essential for maintaining homeostasis of the living body. However, since the animals including human cannot synthesize n-3 series PUFAs inside of the body, it is very important to take n-3 series PUFAs orally. Therefore, when uptake of n-3 series PUFAs from food is deficient, it is desired to supplement with the food additives or the food additives for animals. The fatty acid extracted from the transformant mentioned above can be utilized as PUFAs for the purpose as mentioned above.

In addition, when n-3 series PUFAs extracted from the transformant described above is supplemented, not only the content rate of supplemented PUFAs but also the content rate of the downstream metabolite can be increased. For example, when α-linolenic acid is supplemented, not only α-linolenic acid but also the content rates of the downstream products such as docosahexaenoic acids (DHA) and prostaglandins can be increased. Since docosahexaenoic acids is necessary for baby's brain development, the fatty acid extracted from the tranformant mentioned above is useful as the powered milk or the food additives for child care.

(4-7) Detection Device

The present invention provides various detection device. The detection device according to the present invention is the one that the polynucleotide or the fragment of the present invention is fixed on the substrate, or that the polypeptide or the antibody of the present invention is fixed on the substrate. It can be utilize for detection and measurement of expression pattern of the polynucleotide and the polypeptide of the present invention under various conditions.

When used in the specification, the term "substrate" intends to a substance able to support objects (for example, polynucleotide, oligonucleotide, polypeptide or protein), and can be used interchangeably for the term "support medium". Preferable substrate (or support medium) includes, but is not limited to, the bead (for example, polystyrene bead) and the solid phase (for example, glass tube, the reagent strip, polystyrene microtiter plate or amino radical bound type microtiter plate), etc. The method for fixation of the objects on these substrates is well-known in the persons skilled in the art, and is described in, for example, Nature 357: 519-520 (1992), which is incorporated by reference in the specification.

In one embodiment, the detection device according to the present invention is characterized in fixation of the polynucleotide and/or the oligonucleotide of the present invention on the substrate. In a preferable aspect of the embodiment, the detection device according to the embodiment is a so-called DNA chip. When used in the specification, the term "DNA tip" means a synthetic DNA tip, wherein synthesized oligonucleotide is fixed on the substrate, but it is not limited to this meaning. It also encompasses a stick-on type DNA microarray, wherein cDNA such as PCR product is fixed on the substrate. For DNA chip, for example, included is DNA chip, wherein the probe that specifically hybridizes to the gene of the present invention, i.e., the oligonucleotide of the present invention is fixed on the substrate (carrier).

The sequence used as a probe can be determined according to the publicly known method of specifying a characteristic sequence from cDNA sequence (for example, but it is not limited to, the SAGE method (Serial Analysis of Gene Expression method) (Science 276: 1268, 1997; Cell 88: 243, 1997; Science 270: 484, 1995; Nature 389: 300, 1997; U.S. Pat. No. 5,695,937) etc.).

In addition, manufacture of DNA tip is utilized in the publicly known method. For example, when synthetic oligonucleotide is used as oligonucleotide, by combination of fitriography technology and solid phase-DNA synthesis techniques, oligonucleotide may be synthesized on the substrate. On the other hand, when cDNA is used as oligonucleotide, it only has to stick it on the substrate with an array machine.

Moreover, the detection accuracy of polynucleotide may be further improved by arranging the mismatch probe for which one base is substituted in the perfect match probe (oligonucleotide) and the perfect match probe for example. In addition, to detect different polynucleotide in parallel, DNA tip, wherein plural kinds of oligonucleotides are fixed on the same substrate, may be constituted.

Any material for the substrate used in the detection device of the embodiment can be utilized as long as it can stably fix the polypeptide or the antibody. The substrate other than that described above includes, but is not limited to, for example, synthetic resin such as polycarbonate and plastic, glass, and the like. Form of the substrate is not particularly limited. For example, the substrate in the form of plates, films, etc. can preferably be used. In a preferable aspect of the embodiment, the detection device of the embodiment is used for detecting cDNA library prepared from various organisms, or tissues or cells therefrom as a target sample.

In another embodiment, the detection device according to the present invention is characterized by fixing the polypeptide or the antibody of the present invention on the substrate. In a preferable aspect of the embodiment, the detection device of the embodiment is a so-called protein chip.

Any material for the substrate used in the detection device of the present invention can be utilized as long as it can stably fix the polypeptide or the antibody. The material other than that described above includes, but is not limited to, for example, synthetic resin such as polycarbonate and plastic, glass, and the like. Form of the substrate is not particularly limited. For example, the substrate in the form of plates, films, etc. can preferably be used.

For the method for fixing the polypeptide or the antibody on the substrate other than the above-mentioned method, for example, included is physical absorption method, wherein the polypeptide or the antibody is spotted on nitrocellulose membrane or PVDF membrane in the similar way to dot blotting, or a method for spotting the polypeptide or the antibody on a pad of polyacrylamide onto slide glass to reduce denaturation of the polypeptide or the antibody. In addition, a method using the aldehyde modification glass (G. MacBeath, S. L. Schreiber, Science, 289, 1760 (2000)) for not only adsorption of the polypeptide or the antibody on the surface of substrate, but also rigid binding, can be used. Moreover, as a method of the arrangement for the distribution of the polypeptide on the substrate and the fixation, the method, wherein the polypeptide is fixed via oligo-histidine-tag on the surface-modified substrate by nickel complex, can be used (H. Zhu, M. Bilgin, R. Bangham, D. Hall, A. Casamayor, P. Bertone, N. Lan, R. Jansen, S. Bidlingmaier, T. Houfek, T. Mitchell, P. Miller, R. A. Dean, M. Gerstein, M. Snyder, Science, 293, 2101 (2001)).

In a preferable aspect of the embodiment, the detection device according to the embodiment is used for the detection in the case that makes the extract from various organisms or, tissues or cells therefrom a target sample.

Thus, the detection device of the present invention may be one, wherein at least the polynucleotide or the oligonucleotide according to the present invention, the polypeptide of the present invention or the antibody bound to the polypeptide is fixed on the support medium. Moreover, it can be said that the detection device of the present invention may provide a substrate, on which the polynucleotide or the oligonucleotide according to the present invention, the polypeptide of the present invention or the antibody bound to the polypeptide is fixed. That is, it is necessary to note the fact included within the technical scope of the present invention when providing with the composition materials other than these support medium (including the substrate).

In a word, since the present invention intends to provide a device that detects the polypeptide of the present invention, the polynucleotide of the present invention, or the polypeptide, to which the antibody of the present invention is bound, its purpose does not exist in the kind of individual support media, and the method of fixation of the individual support medium, which specifically described in the specification. Therefore, it is necessary to note that the detection device where the composition materials other than the above-men-

EXAMPLES

Example 1

Cloning of a Partial Sequence of ω3 Fatty Acid Desaturase by PCR

Figure 1:
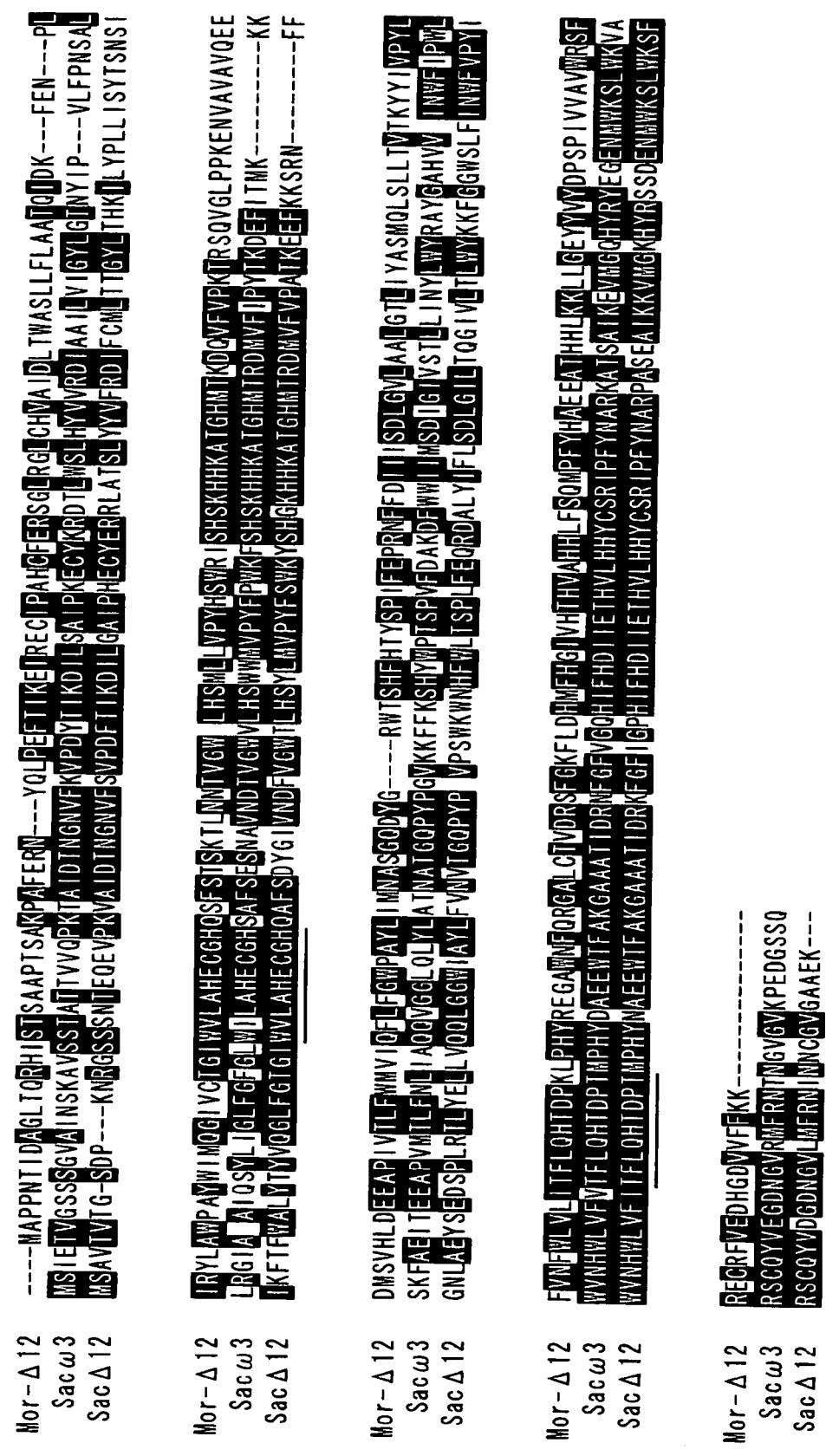

The deduced amino acid sequences of $\Delta^{12}$ fatty acid desaturase of *Mortierella alpina* and *Saccharomyces kluyveri* and ω3 fatty acid desaturase of *S. kluyveri* were compared and the primer corresponding to a highly homologous amino acid sequence was designed. FIG. 1 shows the deduced amino acid sequences of $\Delta^{12}$ fatty acid desaturase of *Mortierella alpina* and *Saccharomyces kluyveri* and ω3 fatty acid desaturase of *S. kluyveri*. In the figure, the upper row shows the deduced amino acid sequence of $\Delta^{12}$ fatty acid desaturase of *M. alpina* (SEQ ID NO: 10), and the central row shows the deduced amino acid sequence of ω3 fatty acid desaturase of *S. kluyveri* (SEQ ID NO: 11) and the lower shows the deduced amino acid sequence of $\Delta^{12}$ fatty acid desaturase of *S. kluyveri* (SEQ ID NO: 12). Primers ω3-F1 and ω3-R1 consisting of degenerated oligonucleotide corresponding to the highly homologous amino acid sequence, which are underlined in the figure, were designed.

ω3-F1 (the corresponding amino acid sequence: WVLA-HECGH; primer is forward):

```
5'-TGGGTIYTBGCICAYGARTGYGGHCA-3'    (SEQ ID NO: 4)
```

ω3-R1 (the corresponding amino acid sequence: TFLQHT-DPK; primer is reverse):

```
5'-TTIGGRTCIGTRTGYTGVARRAAIGT-3'    (SEQ ID NO: 5)
```

Herein, in the base sequence of the above-mentioned primers, "I" shows inosine, "Y" shows T (thymine) or C (cytosine), "B" shows G (guanine), C or T, "R" shows G or A (adenine), "H" shows A, C or T, and "V" shows A, G or C. In addition, the above-mentioned "I" is shown by "n" in SEQ ID NO: 4 and SEQ ID NO:5.

*M. alpina* (1S-4 strain) genomic DNA was prepared according to the method by Sakuradani et al., 1999a, $\Delta^9$-Fatty acid desaturase from arachidonic acid-producing fungus. Unique gene sequence and its heterologous expression in a fungus, *Aspergillus*. Eur J Biochem, 260: 208-216.

PCR was performed by using the obtained *M. alpina* genomic DNA as a template, and using the above-mentioned primers ω3-F1 and ω3-R1. PCR was performed by a reaction of 94° C. for 3 minutes, 30 cycles by 94° C. for 1 minute, 55° C. for 1 minute and 72° C. for 1 minute, and 72° C. for 10 minutes using ExTaq (Takara Bio). The PCR reaction was performed in the reaction mixture of 50 μl in total volume containing 1 μg of genomic DNA, 0.25 μl of Takara Ex Taq polymerase (Takara Bio), 5 μl of 10× Ex Taq buffer, 200 μM each of dNTP, and 200 pmol each of the primers. Herein, when the PCR products were analyzed by agarose gel electrophoresis, one band for fragment of about 600 bp was detected. Since under the PCR conditions used, a DNA fragment, which was amplified using $\Delta^{12}$ fatty acid desaturase gene as a template, forms about 600 bp band, it was considered that the fragment was a mixture of the sequence derived from ω3 fatty acid desaturase gene and the fragment derived from $\Delta^{12}$ fatty acid desaturase gene. Thus the DNA fragment was digested with restriction enzyme KpnI, which cleaves $\Delta^{12}$ fatty acid desaturase gene (the sequence has been clarified) at one site, and analyzed again by agarose gel electrophoresis. As a result, a DNA fragment of the original size and two DNA fragments of shorter size than the original size were obtained, and it was demonstrated that PCR products were a mixture of DNA fragment derived from $\Delta^{12}$ fatty acid desaturase gene and another DNA fragment.

Then, the fragment which was not digested with KpnI was purified among the PCR products, and was ligated with pT7Blue T-vector (Novagen) by ligation high (Toyobo) (all TA clonings were also performed similarly). Analysis of the base sequence was done with ABI3100 (Applied Biosystems). Homology search was performed to the amino acid sequence registered in GenBank using blastx. As a result, the base sequence demonstrated the highest homology to that of $\Delta^{12}$ fatty acid desaturase gene derived from *M. alpina* (1S-4 strain), and in particular, the identity of the base sequence in the region was 57%.

Example 2

Determination of Genomic DNA Sequence of ω3 Fatty Acid Desaturase

Based on the base sequence of about 600bp, which was obtained, the following primers were designed, and Inverse PCR (reverse-PCR) was performed.

```
                                    (SEQ ID NO: 6)
ω3-IPCRR2:  5'-GACCCATCCAAAGATGGTGTTGATC-3'

(SEQ ID NO: 7)
ω3-IPCRF2:  5'-GACTGTCTTCATGTACTATGGCATC-3'
```

First of all, genomic DNA prepared from *Mortierella alpina* was digested completely with EcoRI, and then reacted at 15° C. for overnight using ligation high (Toyobo), consequently the DNA fragment was closed by self-ligation. PCR was performed by using the above-mentioned DNA as a template and using primers ω3-IPCRF2 and ω3-IPCRR2 described above. The PCR reaction mixture was the same as that of Example 1 except for concentration of the template, which was 50 ng/μl. PCR was performed by a reaction of 94° C. for 3 minutes, 35 cycles for 94° C. for 1 minute, 60° C. for 2 minutes and 72° C. for 3 minutes, and 72° C. for 15 minutes by using ExTaq (Takara Bio).

The obtained DNA fragment of 3-4 kb was TA cloned into vector pT7Blue T-vector (Novagen) according to the method similar to Example 1. The base sequence of several hundreds bp from both terminus of the ca. 4 kb fragment was determined. Then the fragment was ligated with the partial sequence previously obtained. This base sequence is shown in SEQ ID NO: 2. The coding region of ω3 fatty acid desaturase gene was deduced by comparison with homologous sequences, appearance of an initiation codon and a termination codon, etc. It was considered that the coding region was the base from 14 to 1366, and the gene had an intron.

Example 3

Cloning of cDNA of ω3 Fatty Acid Desaturase

It had been clarified that ω3 fatty acid desaturase is expressed by the low temperature culture. Thus, *M. alpina* (IS-4 strain) was cultured in GY liquid medium at 28° C. for 7 days followed by further culture at 12° C. for 2 days. Then the bacterial cell was harvested. According to the method of Sakuradani et al., 1999a, $\Delta^9$-Fatty acid desaturase from arachidonic acid-producing fungus. Unique gene sequence and its heterologous expression in a fungus, *Aspergillus*. Eur J Biochem 260: 208-216, total RNA was extracted. For 1 µg of total RNA, using 1 st-Strand cDNA Synthesis Kit for RT-PCR (AMV) (Roche Diagnostics Corporation), a reverse transcription reaction was performed with random hexamer as a primer to synthesize cDNA. Using the synthesized cDNA as a template and primers ω3-ExF3 and ω3-ExR3 described below, PCR was performed. The PCR reaction was performed using a reaction mixture of 50 µl in total volume containing 1 µg of template cDNA, 0.25 µl of Takara LA Taq polymerase (Takara Bio), 5 µl of 10× LA Taq buffer, 2 mM $MgCl_2$, 200 µM each dNTP and 100 pmol each of primers. Moreover, the reaction condition for PCR is as follows: 94° C. for 3 minutes, 35 cycles for 94° C. for 1 minute, 60° C. for 2 minutes and 72° C. for 3 minutes, and 72° C. for 15 minutes.

(SEQ ID NO: 8)
ω3-ExF3: 5'-CAGAGTCATAaagcttAAatgGCCCCCCCT-3'

(SEQ ID NO: 9)
ω3-ExR3: 5'-GACgcatgcCGTATTCAAATTGttaTTAATGC-3'

Herein, primer ω3-ExF3 contains ATG initiation site (shown by lower case in the sequence) and HindIII cloning site: aagctt (shown by lower case in the sequence). Moreover, primer ω3-ExR3 contains TAA termination site (shown by lower case in the sequence) and SphI cloning site: gcatgc (shown by lower case in the sequence).

The DNA fragment obtained was cloned into vector pT7Blue T-vector (Novagen) by TA cloning according to the method similar to the method described in Example 1. Then the base sequence was determined. The base sequence of cDNA that was determined is shown as SEQ ID NO: 3. The base sequence of cDNA was identical to 1212 bp consisting of 330 bp from the 14th base to the 343rd base and 882 bp from the 485th base to the 1366th base of the base sequence of genomic DNA determined in Example 2 described above (SEQ ID NO: 2). From this result, it was found that 1353 bp from the 14th base to the 1366th base of the base sequence represented by SEQ ID NO: 2 corresponds to ω3 fatty acid desaturase gene, and that this gene contain the intron that consists of 141 bp from the 345th base to the 485th base of the base sequence represented by SEQ ID NO: 2, and encodes 403 amino acids.

Figure 2:
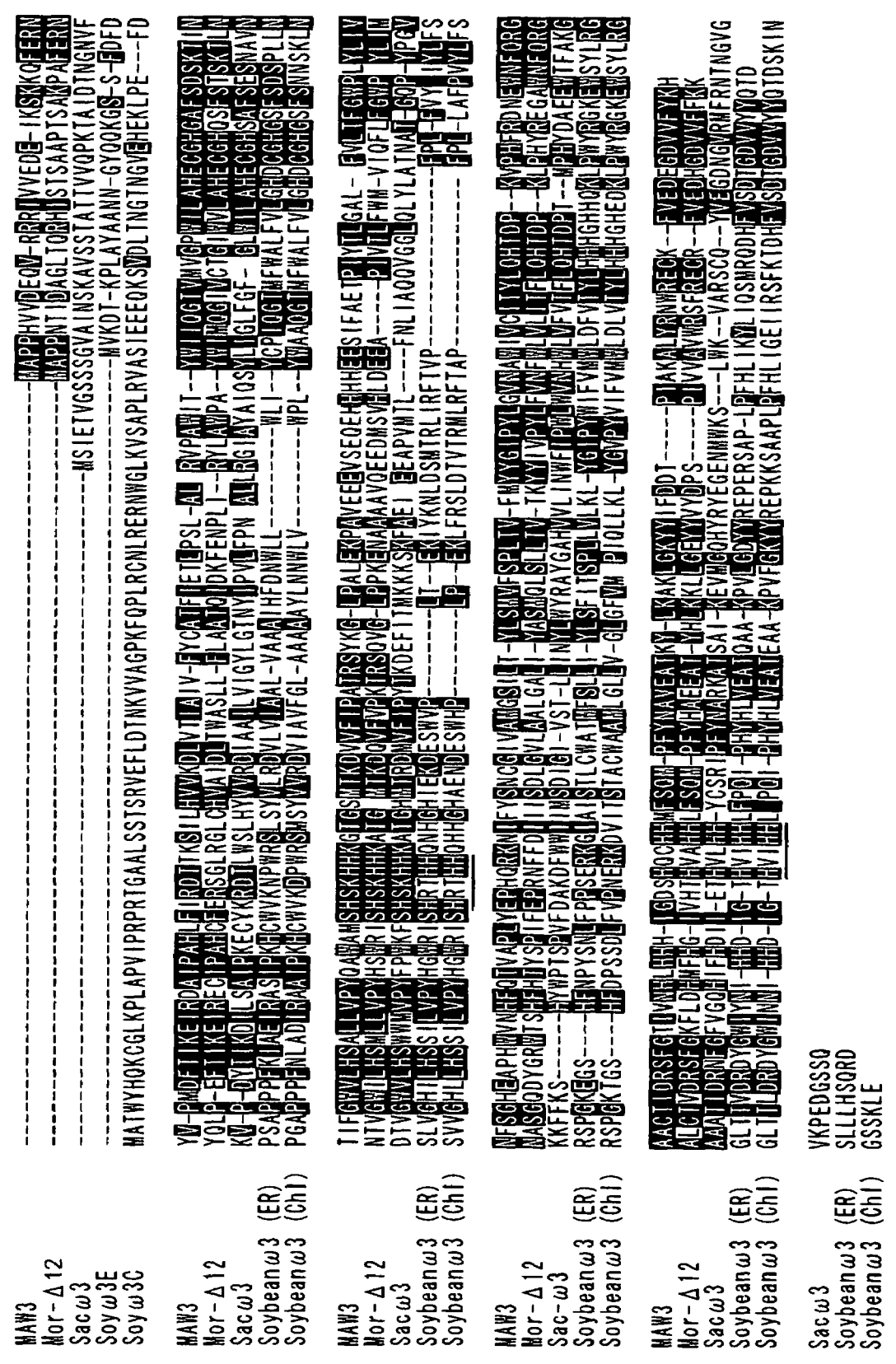

The amino acid sequence encoded by the cDNA was compared with the amino acid sequence of known ω3 fatty acid desaturase of other species and $\Delta^{12}$ fatty acid desaturase of *M. alpina*. In FIG. 2, the amino acid sequences for ω3 fatty acid desaturase of *M. alpina* (referred to as "MAW3" in the figure; SEQ ID NO: 1), $\Delta^{12}$ fatty acid desaturase of *M. alpina* (referred to as "Mor-Δ12" in the figure; SEQ ID NO: 10), ω3 fatty acid desaturase of *S. kluyveri* (referred to as "Sacω3" in the figure; SEQ ID NO: 11), endoplasmic reticulum-localized ω3 fatty acid desaturase of soybean (referred to as "Soybeanω3 (ER)" in the figure; SEQ ID NO: 13) and chloroplast-localized ω3 fatty acid desaturase of soybean (referred to as "Soybeanω3 (Chl)"; SEQ ID NO: 14) are shown beginning at the top. The amino acid sequence of the ω3 fatty acid desaturase of *M. alpina* had the identity of 51%, 36%, 34%, and 32% to those of $\Delta^{12}$ fatty acid desaturase of *M. alpina*, ω3 fatty acid desaturase of *S. kluyveri*, endoplasmic reticulum-localized ω3 fatty acid desaturase of soybean, and chloroprast-localized ω3 fatty acid desaturase of soybean, respectively. As shown in FIG. 2, it was found that the ω3 fatty acid desaturase of *M. alpina* shows only a low identity (36% identity even if the case of *S. kluyveri*, wherein the amino acid sequence is the most similar in the ω3 fatty acid desaturases). From this result, it was found that the amino acid sequence of ω3 fatty acid desaturase of *M. alpina* is similar to that of $\Delta^{12}$ fatty acid desaturase of *M. alpina* own rather than the amino acid sequences of known ω3 fatty acid desaturase of other species.

Example 4

Construction of Expression Vector for ω3 Fatty Acid Desaturase Gene

The expression vector to make obtained cDNA coding for the ω3 fatty acid desaturase derived from *M. alpina* (1S-4 strain) expressed in yeast was constructed.

DNA fragment obtained in Example 3 was treated with HindIII-SphI, and was ligated with the HindIII-SphI site of yeast expression vector pYES2 (Invitrogen) to construct plasmid pYMAW3. The pYMAW3 is a construct, wherein 1212 bp that is the entire cDNA of ω3 fatty acid desaturase was inserted into the HindIII-SphI site of pYES2.

Example 5

Transformation of Yeast Using an Expression Vector

Yeast *Saccharomyces cerevisiae* INVSc1 (Invitrogen) was transformed by the plasmid pYMAW3 to obtain transformants ω3-1 and ω3-2. Transformation was performed using electroporation method according to the method of Ausubel F M, Brent R, Kingston R E, Moore D D, Seidman J G, Smith J A, Struht k., (1994) Transformation by electroporation. In Current protocols in Molecular Biology. pp. 13.7.5.-13.7.7., Green Publishing Associates and Wiley-Interscience, New York. The transformant was selected by tryptophan requirement as an index using YNBD(-Trp) medium.

Example 6

Expression of ω3 Fatty Acid Desaturase Gene and Functional Analysis

First of all, liquid medium containing 2% raffinose (Difco), 2% polypeptone (Daigo) and 1% yeast extract (Difco) was autoclaved. Then as the substrate that enables detection of the ω3 fatty acid desaturase activity, linoleic acid (LA; 18:2$\Delta^{9,12}$), which is n-6 series fatty acid, γ-linolenic acid (GLA; 18:3$\Delta^{6,9,12}$), which is n-6 series fatty acid, dihomo-γ-linolenic acid (DGLA; 20:3$\Delta^{8,11,14}$), which is n-6 series fatty acid, or methyl ester of arachidonic acid (AA or ARA; 20:4$\Delta^{5,8,11,14}$), which is n-6 series fatty acid, was added to the medium to make its concentration 0.1% (v/w), respectively. To each medium, one platinum loop of transformant was inoculated and cultured with shaking at 28° C. at 300 rpm for 24 hours. In addition, Yeast INVScl containing the unmodified pYES2 vector was used as a control.

Subsequently, to express ω3 fatty acid desaturation gene, galactose was added to the medium to be 2% in the final concentration, and further, the shaking culture was done at 28° C. at 309 rpm for 48 hours.

Example 7

Detection of ω3 Fatty Acid Desaturation Activity

To detect ω3 fatty acid desaturation activity, fatty acid of the entire cell was analyzed. The fatty acid analysis was performed according to the method of Sakuradani et al.1999a, $\Delta^9$-Fatty acid desaturase from arachidonic acid-producing fungus. Unique gene sequence and its heterologous expression in a fungus, *Aspergillus*; Eur J Biochem 260: 208-216.

Yeast cell was harvested by centrifugation, and after washing by distilled water, it was dried at 100° C. The dried cell was stood for three hours at 50° C. after adding methanol containing 10% hydrogen chloride to transfer methyl radical directly. In such ways, fatty acid residue in the yeast cell was induced into a methyl ester by the hydrochloric acid-methanol method, followed by extraction with hexane. Then methyl ester of fatty acid obtained after removal of hexane was analyzed by gas chromatography.

The result is shown in Table 1. Herein, in the table, the strain represented by "pYES2" shows a control strain including unmodified pYES2 vector. Further, "ω3-1" and "ω3-2" show two independent experiments that was performed by using different transformants. "Substrate (%)" represents a molar composition of the substrate (e.g., linoleic acid (LA; $18:2\Delta^{9,12}$), which is n-6 series fatty acid) in the total fatty acid detected. "Product (%)" represents a molar composition of ω3 unsaturated product (e.g., α-linolenic acid (ALA; $18:3\Delta^{9,12,15}$), which is n-3 series fatty acid, when the substrate was LA) in the total fatty acid detected. Moreover, "Conversion rate (%)" was calculated by using a equation: Product (%)/(Substrate (%)+Product (%))×100. Further, in the control strain containing the unmodified pYES2 vector, the fatty acid added as a substrate had not been converted at all.

TABLE 1

| Strain | Substrate | Substrate (%) | Product | Product (%) | Conversion rate (%) |
|---|---|---|---|---|---|
| pYES2 | 18:2n-6 | 13.2 | 18:3n-3 | 0.0 | 0 |
|  | 18:3n-6 | 19.4 | 18:4n-3 | 0.0 | 0 |
|  | 20:3n-6 | 7.0 | 20:4n-3 | 0.0 | 0 |
|  | 20:4n-6 | 8.3 | 20:5n-3 | 0.0 | 0 |
| ω3-1 | 18:2n-6 | 10.8 | 18:3n-3 | 1.4 | 11.6 |
|  | 18:3n-6 | 17.3 | 18:4n-3 | 1.9 | 9.8 |
|  | 20:3n-6 | 5.8 | 20:4n-3 | 0.3 | 5.4 |
|  | 20:4n-6 | 3.9 | 20:5n-3 | 0.4 | 9.1 |
| ω3-2 | 18:2n-6 | 9.3 | 18:3n-3 | 1.9 | 16.9 |
|  | 18:3n-6 | 10.3 | 18:4n-3 | 2.6 | 20.1 |
|  | 20:3n-6 | 7.1 | 20:4n-3 | 0.3 | 4.2 |
|  | 20:4n-6 | 9.0 | 20:5n-3 | 0.2 | 2.4 |

As shown in Table 1, when the ω3 fatty acid desaturase gene derived from *M. alpina* (1S-4 strain) is expressed in yeast, it was confirmed that ω3 position of all added kinds of n-6 series fatty acid having 18 and 20 carbons can be unsaturated to generate n-3 series fatty acid. That is, linoleic acid (LA; $18:2\Delta^{9,12}$), which is n-6 series fatty acid, was converted to α-linolenic acid (ALA; $18:3\Delta^{9,12,15}$), which is n-3 fatty acid. γ-linolenic acid (GLA; $18:3\Delta^{6,9,12}$), which is n-6 series fatty acid, is converted to stearidonic acid ($18:4\Delta^{6,9,12,15}$), which is n-3 series fatty acid. Dihomo-γ-linolenic acid (DGLA; $20:3\Delta^{8,11,14}$), which is n-6 series fatty acid, is converted to $20:4\Delta^{8,11,14,17}$, which is n-3 series fatty acid. Arachidonic acid (AA or ARA; $20:4\Delta^{5,8,11,14}$), which is n-6 series fatty acid, is converted to eicosapentaenoic acid (EPA; $20:5\Delta^{5,8,11,14,17}$), which is n-3 series fatty acid. Since no other novel fatty acid was detected, it was found that the ω3 fatty acid desaturase gene does not have a $\Delta^{12}$ fatty acid desaturation activity, a $\Delta^6$ fatty acid desaturation activity and/or a $\Delta^5$ fatty acid desaturation activity.

Moreover, from the results of Table 1, it was shown that the ω3 fatty acid desaturase derived from *M. alpina* (1S-4 strain) is able to desaturate n-6 series fatty acid having 18 and 20 carbons at ω3 position, in particular, ω3 position of n-6 series fatty acid having 18 carbons can be unsaturated more efficiently as compared with the case of n-6 series fatty acid having 20 carbons.

Figure 4:
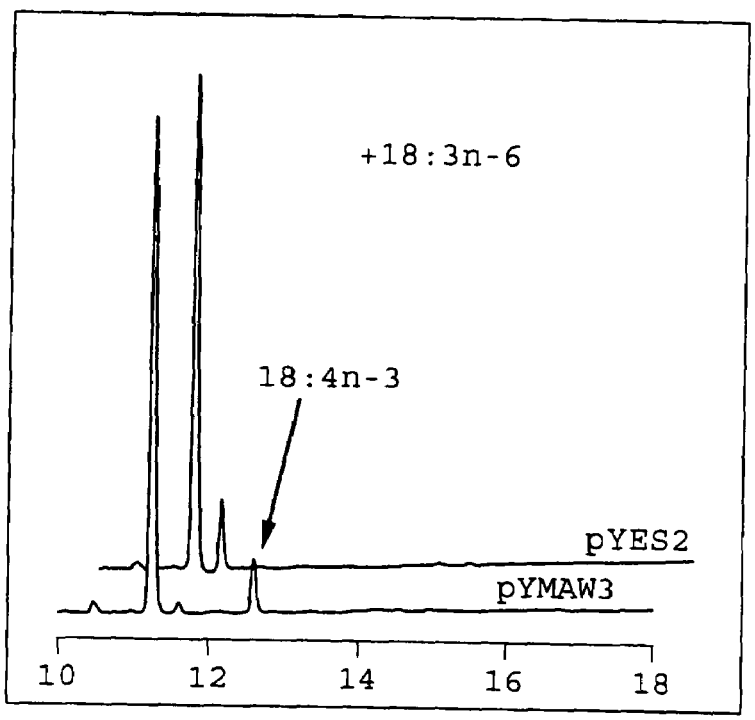
FIG. 4 shows a result of fatty acid analysis by gas chromatography in yeast *Saccharomyces cerevisiae*, in which pYMAW3 was introduced, in the case where γ-linolenic acid was added as a substrate.
Figure 5:
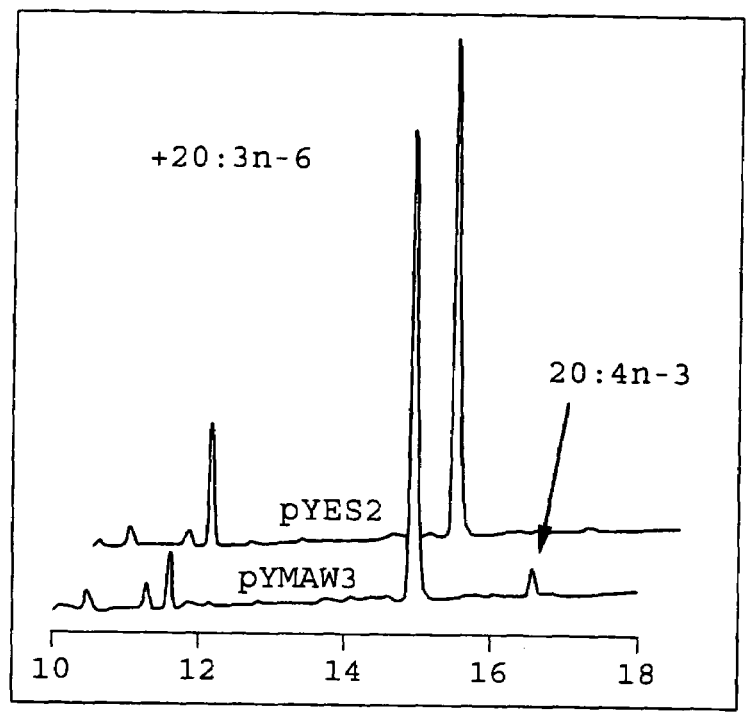
FIG. 5 shows a result of fatty acid analysis by gas chromatography in yeast *Saccharomyces cerevisiae*, in which pYMAW3 was introduced, in the case where dihomo-γ-linolenic acid was added as a substrate.
Figure 6:
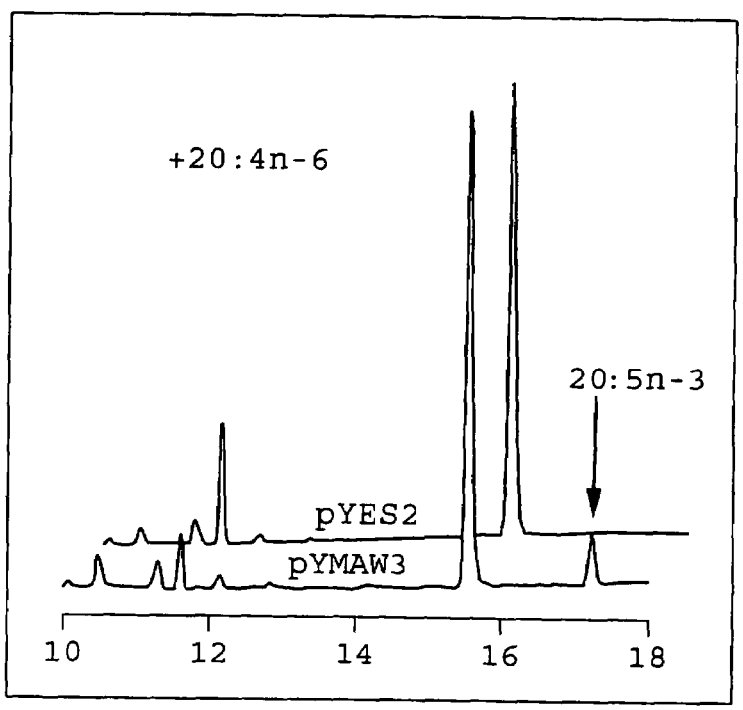
FIG. 6 shows a result of fatty acid analysis by gas chromatography in yeast *Saccharomyces cerevisiae*, in which pYMAW3 was introduced, in the case where arachidonic acid was added as a substrate.

FIGS. 3 through 6 show results of the fatty acid analysis by gas chromatography. FIG. 3 represents a result of the analysis when linoleic acid is added. FIG. 4 represents a result of the analysis when γ-linolenic acid is added. FIG. 5 represents a result of the analysis when dihomo-γ-linolenic acid is added. FIG. 6 represents a result of the analysis when arachidonic acid is added. In these figures, novel peaks derived from n-3 series fatty acid, which was generated by unsaturation of n-6 series fatty acid at ω3 position, are found. Moreover, these peaks are not observed in a result of the analysis for the control strain shown in the same figure. The fatty acid ester detected as a new peak was identified by comparison with retention time of standard substance, molecular ion peak and fragmentation pattern obtained by GLC-MS analysis.

Example 8

Expression of ω3 Fatty Acid Desaturase gene in Yeast Under Low Temperature Condition and Functional Analysis Using the transformant ω3-1, wherein the yeast INVSc1 (Invitrogen) was transformed with plasmid pYMAW3 obtained in Example 4, ω3 fatty acid desaturase gene was expressed under low temperature condition.

To liquid media consisting of 2% raffinose (Difco), 2% polypepton (Daigo) and 1% yeast extract (Difco) after autoclaving, the same substrate as that of Example 6 was added in 0.05% (v/w). To each medium, one platinum loop of the transformant was inoculated and cultured with shaking at 28° C. at 300 rpm for 24 hours. Subsequently, galactose was added to the medium to be 2% in the final concentration, and further, the shaking culture was done at 20° C. or 12° C. at 300 rpm for 48 hours.

As for the analysis of control and a fatty acid methyl ester, it was performed in similar way to Example 5. Table 2 below shows the result. The fatty acid added as a substrate had not been converted in each temperature in the control strain that was transformed by the unchanged pYES2 vector, though it was not shown in the table. As for "Substrate (%)", "Product (%)", and "Conversion rate (%)", it is as explained in Example 7.

TABLE 2

| | Conversion rate (%) | | | |
|---|---|---|---|---|
| Reaction Temperature | 18:2n-6 → 18:3n-3 | 18:3n-6 → 18:4n-3 | 20:3n-6 → 20:4n-3 | 20:4n-6 → 20:5n-3 |
| 28° C. | 2.3 | 7.8 | 2.4 | 2.1 |
| 20° C. | 19.0 | 30.9 | 8.7 | 4.6 |
| 12° C. | 30.1 | 45.9 | 19.8 | 14.7 |

As shown in Table 2, even when which substrate was added, it was confirmed that the conversion rate in low temperature condition at 20° C. or 12° C. was several times higher than that at 28° C. From this result, it was found that ω3 fatty acid desaturase derived from *M. alpina* (1S-4 strain) is an enzyme that functions more efficiently at low temperature.

The present invention is not limited to the above-described embodiment, and is possible to change in various ways within the scope of the claims. That is, the embodiment obtained in combination with appropriately modified technical means within the scope of the claims is encompassed into the technical scope of the present invention.

INDUSTRIAL APPLICABILITY

As mentioned above, the polypeptide and the polynucleotide according to the present invention are useful for production of n-3 series fatty acid. Moreover, in a food field and various industrial fields, the transformant or the cell, in which the polynucleotide according to the present invention was expressibly introduced, is extremely useful for production of n-3 series fatty acids or the products using the same. Further, in particular, when the above-mentioned transformant is a plant, it is very useful in agricultural field etc., because the plant can be used as a food.

The invention claimed is:

1. An isolated polynucleotide coding for a polypeptide having an ω3 fatty acid desaturation activity, which is:
   (a) a polypeptide consisting of the amino acid sequence represented by SEQ ID NO: 1, or
   (b) a polypeptide consisting of an amino acid sequence, wherein one to 10 amino acids are substituted, deleted, inserted, or added in the amino acid sequence represented by SEQ ID NO: 1.

2. An isolated polynucleotide coding for a polypeptide having a ω3 fatty acid desaturation activity, which is any of (c), (d), (e) or (f) described below:
   (c) a polynucleotide consisting of the base sequence represented by SEQ ID NO: 2 or SEQ ID NO: 3;
   (d) a polynucleotide consisting of the base sequence from 14 to 1366 of the base sequence represented by SEQ ID NO: 2;
   (e) a polynucleotide having at least 90% sequence identity to the base sequence represented by SEQ ID NO: 2 or SEQ ID NO: 3
   (f) a polynucleotide having at least 90% sequence identity to the base sequence from 14 to 1366 of the base sequence represented by SEQ ID NO: 2.

3. A vector comprising the polynucleotide of claim 1.

4. A non-human transformant, wherein the polynucleotide of claim 1 is introduced.

5. The transformant of claim 4, which is fungus, animal, plant or progeny thereof, or a cell or tissue therefrom.

6. The transformant of claim 5, wherein the plant is soybean, rapeseed, sesame, olive, linseed, maize, sunflower or safflower.

7. The transformant of claim 4, wherein composition of the fatty acid is modified.

8. A method for producing a polypeptide, comprising using the vector of claim 3.

9. A method for producing a polypeptide, comprising using the transformant of claim 4.

* * * * *

UNITED STATES PATENT AND TRADEMARK OFFICE
CERTIFICATE OF CORRECTION

PATENT NO. : 7,615,364 B2  Page 1 of 1
APPLICATION NO. : 11/660093
DATED : November 10, 2009
INVENTOR(S) : Shimizu et al.

It is certified that error appears in the above-identified patent and that said Letters Patent is hereby corrected as shown below:

Title page, title and Col. 1, line 5

Item (54) should read:

POLYPEPTIDE HAVING ACTIVITY OF UNSATURATING ω3-FATTY ACID, POLYNUCLEOTIDE CODING FOR THE POLYPEPTIDE AND USE THEREOF

Signed and Sealed this

Nineteenth Day of January, 2010

David J. Kappos
*Director of the United States Patent and Trademark Office*